(12) United States Patent
Franke et al.

(10) Patent No.: US 8,147,642 B2
(45) Date of Patent: Apr. 3, 2012

(54) PROCESS OF MAKING BOXER SHORTS FROM A WEB

(75) Inventors: Mark Steven Franke, Neenah, WI (US); Heather Schenck Mortell, Neenah, WI (US); Joseph Daniel Coenen, Kaukauna, WI (US); Robert Lee Popp, Hortonville, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 182 days.

(21) Appl. No.: 10/954,628

(22) Filed: Sep. 30, 2004

(65) Prior Publication Data

US 2005/0120465 A1    Jun. 9, 2005

Related U.S. Application Data

(63) Continuation-in-part of application No. 10/314,915, filed on Dec. 9, 2002.

(51) Int. Cl.
*B29C 65/48* (2006.01)
*B32B 37/02* (2006.01)
*B32B 38/04* (2006.01)

(52) U.S. Cl. ........ 156/257; 156/196; 156/204; 156/227; 156/160; 156/200; 156/211; 156/221; 156/265; 156/270; 156/226; 156/229

(58) Field of Classification Search .................. 156/256, 156/160, 200, 211, 221, 265, 270, 226, 229, 156/257, 269, 196, 204, 199, 227; 604/366
See application file for complete search history.

(56) References Cited

U.S. PATENT DOCUMENTS

| | | | |
|---|---|---|---|
| 478,281 | A | 7/1892 | Hamilton et al. |
| 1,577,409 | A | 3/1926 | Rand |
| 1,664,298 | A | 3/1928 | Katz |
| 1,971,558 | A | 8/1934 | Goodman |
| 2,030,306 | A | 2/1936 | Lain |
| 2,032,982 | A | 3/1936 | Gerstman |
| 2,088,302 | A | 7/1937 | McKeever |

(Continued)

FOREIGN PATENT DOCUMENTS

AT    168478 B    6/1951

(Continued)

OTHER PUBLICATIONS

Printed materials (3 pages) showing pull-on diapers disclosed at a trade show Apr. 27-29, 2004 in Miami Beach, Florida, U.S.A.

(Continued)

*Primary Examiner* — Linda L Gray
(74) *Attorney, Agent, or Firm* — Armstrong Teasdale LLP

(57) ABSTRACT

A boxer-style pant and a method of making a boxer-style pant having side seams, a contracted crotch region, and hanging legs. A web is provided. The web may be a single pant assembly, or a continuous web of multiple pant assemblies connected to one another. The web may be folded against a support structure. In certain embodiments, a multi-lane production system may be used wherein the web is folded against multiple support structures each parallel to a direction in which the web is conveyed, with each lane or machine direction array of pant assemblies folded against just one support structure. The web is cut to define leg openings, and contracted in selected areas along the web between the leg openings. Front and back regions are then joined together to form the side seams. An absorbent structure may be attached to the web.

15 Claims, 18 Drawing Sheets

U.S. PATENT DOCUMENTS

| | | | |
|---|---|---|---|
| 2,116,822 A | 5/1938 | Berger | |
| 2,131,808 A * | 10/1938 | Joa | 19/145 |
| 2,242,526 A | 5/1941 | Kneibler | |
| 2,252,019 A | 8/1941 | Meinecke et al. | |
| 2,319,138 A | 5/1943 | Kneibler | |
| 2,391,641 A | 12/1945 | O'Hem | |
| 2,435,945 A | 2/1948 | Redmond | |
| 2,450,789 A | 10/1948 | Frieman | |
| 2,522,510 A | 9/1950 | Fridolph | |
| 2,538,596 A | 1/1951 | Sheridan | |
| 2,675,806 A | 1/1954 | Bram | |
| 2,711,735 A | 6/1955 | Sabo | |
| 2,838,047 A | 6/1958 | Sidnell | |
| 2,842,129 A | 7/1958 | Emstorff | |
| 2,859,752 A | 11/1958 | Haber | |
| 3,245,407 A | 4/1966 | Mason | |
| 3,338,992 A | 8/1967 | Kinney | |
| 3,341,394 A | 9/1967 | Kinney | |
| 3,386,442 A * | 6/1968 | Sabee | 604/366 |
| 3,418,660 A | 12/1968 | Shumate | |
| 3,502,538 A | 3/1970 | Petersen | |
| 3,502,763 A | 3/1970 | Hartmann | |
| 3,542,615 A | 11/1970 | Dobo et al. | |
| 3,611,443 A | 10/1971 | Braun | |
| 3,648,699 A | 3/1972 | Anderson et al. | |
| 3,678,516 A | 7/1972 | Backer | |
| 3,692,618 A | 9/1972 | Dorschner et al. | |
| 3,714,946 A | 2/1973 | Rudes | |
| 3,739,398 A | 6/1973 | Sarmiento | |
| 3,802,817 A | 4/1974 | Matsuki et al. | |
| 3,806,007 A | 4/1974 | Grantham | |
| 3,844,282 A | 10/1974 | King | |
| 3,859,667 A | 1/1975 | Roy | |
| 3,869,999 A | 3/1975 | Richter | |
| 3,920,237 A | 11/1975 | Grantham | |
| 4,059,257 A | 11/1977 | Grantham | |
| 4,081,301 A | 3/1978 | Buell | |
| 4,100,324 A | 7/1978 | Anderson et al. | |
| 4,106,125 A | 8/1978 | Palumbo | |
| 4,114,621 A | 9/1978 | Mims, Jr. | |
| 4,116,892 A | 9/1978 | Schwarz | |
| 4,145,763 A | 3/1979 | Abrams et al. | |
| 4,223,059 A | 9/1980 | Schwarz | |
| 4,227,952 A | 10/1980 | Sabee | |
| 4,280,230 A | 7/1981 | LaFleur | |
| 4,284,454 A | 8/1981 | Joa | |
| 4,285,100 A | 8/1981 | Schwarz | |
| 4,300,241 A | 11/1981 | Shaull | |
| 4,310,929 A | 1/1982 | Finlay | |
| 4,327,448 A | 5/1982 | Lunt | |
| 4,338,939 A | 7/1982 | Daville | |
| 4,340,563 A | 7/1982 | Appel et al. | |
| 4,368,565 A | 1/1983 | Schwarz | |
| 4,392,259 A | 7/1983 | Bredo | |
| 4,397,704 A | 8/1983 | Frick | |
| 4,417,938 A | 11/1983 | Sigl | |
| 4,449,254 A | 5/1984 | Fogg | |
| 4,543,141 A * | 9/1985 | Bradley et al. | 156/164 |
| 4,555,245 A | 11/1985 | Armbruster | |
| 4,597,110 A | 7/1986 | Smith, Sr. et al. | |
| 4,608,115 A | 8/1986 | Schroth et al. | |
| 4,644,945 A | 2/1987 | Thorner | |
| 4,646,362 A | 3/1987 | Heran et al. | |
| 4,650,530 A | 3/1987 | Mahoney et al. | |
| 4,655,760 A | 4/1987 | Morman et al. | |
| 4,663,106 A | 5/1987 | Pomplun et al. | |
| 4,663,220 A | 5/1987 | Wisneski et al. | |
| 4,665,306 A | 5/1987 | Roland et al. | |
| 4,671,793 A | 6/1987 | Hults et al. | |
| 4,675,918 A | 6/1987 | O'Brien | |
| 4,704,116 A | 11/1987 | Enloe | |
| 4,745,636 A | 5/1988 | Lunt | |
| 4,771,483 A | 9/1988 | Hooreman et al. | |
| 4,786,346 A | 11/1988 | Ales et al. | |
| 4,805,243 A | 2/1989 | Gibbens et al. | |
| 4,816,094 A | 3/1989 | Pomplun et al. | |
| 4,835,795 A | 6/1989 | Lonon | |
| 4,847,134 A | 7/1989 | Fahrenkrug et al. | |
| 4,850,992 A * | 7/1989 | Amaral et al. | 604/389 |
| 4,870,958 A | 10/1989 | Webster | |
| 4,872,221 A | 10/1989 | Stone, III | |
| 4,875,240 A | 10/1989 | Barrett | |
| 4,883,549 A | 11/1989 | Frost et al. | |
| 4,892,536 A | 1/1990 | DesMarais et al. | |
| 4,895,568 A | 1/1990 | Enloe | |
| 4,935,021 A | 6/1990 | Huffman et al. | |
| 4,946,539 A | 8/1990 | Ales et al. | |
| 4,955,880 A | 9/1990 | Rodriquez | |
| 4,964,860 A | 10/1990 | Gipson et al. | |
| D315,050 S | 3/1991 | Bush et al. | |
| 5,014,364 A | 5/1991 | Orr | |
| 5,022,240 A | 6/1991 | Peleg | |
| 5,046,272 A | 9/1991 | Vogt et al. | |
| 5,052,058 A | 10/1991 | Mueller | |
| 5,067,178 A | 11/1991 | Katchka | |
| 5,087,253 A | 2/1992 | Cooper | |
| 5,103,505 A | 4/1992 | Llorens | |
| 5,135,522 A | 8/1992 | Fahrenkrug et al. | |
| 5,147,487 A | 9/1992 | Nomura et al. | |
| 5,171,388 A | 12/1992 | Hoffman et al. | |
| 5,187,817 A | 2/1993 | Zolner | |
| 5,210,882 A | 5/1993 | Moretz et al. | |
| 5,217,782 A | 6/1993 | Moretz et al. | |
| 5,226,992 A | 7/1993 | Morman | |
| D341,243 S | 11/1993 | Costella et al. | |
| 5,297,296 A | 3/1994 | Moretz et al. | |
| 5,303,424 A | 4/1994 | Cromartie | |
| 5,306,536 A | 4/1994 | Moretz et al. | |
| 5,315,716 A | 5/1994 | Baum | |
| 5,315,717 A | 5/1994 | Moretz et al. | |
| 5,370,634 A | 12/1994 | Ando et al. | |
| 5,379,462 A | 1/1995 | Morgan et al. | |
| 5,382,246 A | 1/1995 | Kawano | |
| 5,435,014 A | 7/1995 | Moretz et al. | |
| 5,445,628 A | 8/1995 | Gipson et al. | |
| 5,500,063 A | 3/1996 | Jessup | |
| 5,545,158 A | 8/1996 | Jessup | |
| 5,549,593 A | 8/1996 | Ygge et al. | |
| 5,554,149 A | 9/1996 | O'Donnell | |
| 5,556,504 A | 9/1996 | Rajala et al. | |
| 5,566,392 A | 10/1996 | Dzelzkalns | |
| D377,557 S | 1/1997 | Jagger | |
| 5,649,913 A | 7/1997 | Cohen | |
| D382,386 S | 8/1997 | Malone | |
| 5,669,902 A | 9/1997 | Sivilich | |
| 5,669,996 A | 9/1997 | Jessup | |
| 5,690,626 A | 11/1997 | Suzuki et al. | |
| 5,690,627 A | 11/1997 | Clear et al. | |
| 5,704,071 A | 1/1998 | Barclay et al. | |
| 5,716,478 A | 2/1998 | Boothe et al. | |
| 5,718,003 A | 2/1998 | Gwinn | |
| 5,733,401 A | 3/1998 | Linman et al. | |
| 5,746,730 A | 5/1998 | Suzuki et al. | |
| 5,755,902 A | 5/1998 | Reynolds | |
| 5,759,340 A | 6/1998 | Boothe et al. | |
| 5,790,983 A | 8/1998 | Rosch et al. | |
| 5,827,260 A | 10/1998 | Suzuki et al. | |
| 5,843,065 A * | 12/1998 | Wyant | 604/385.09 |
| 5,853,405 A | 12/1998 | Suprise | |
| 5,876,394 A | 3/1999 | Rosch et al. | |
| 5,879,500 A * | 3/1999 | Herrin et al. | 156/204 |
| 5,891,122 A | 4/1999 | Coates | |
| D408,964 S | 5/1999 | Hernandez | |
| 5,906,604 A | 5/1999 | Rönnberg et al. | |
| 5,906,879 A | 5/1999 | Huntoon et al. | |
| 5,907,872 A | 6/1999 | Alberts et al. | |
| 5,921,974 A | 7/1999 | Kikuchi | |
| 5,953,754 A | 9/1999 | Rosch et al. | |
| 5,956,774 A | 9/1999 | Mackley | |
| 5,978,971 A | 11/1999 | Wald | |
| D417,940 S | 12/1999 | Coates et al. | |
| 6,009,558 A | 1/2000 | Rosch et al. | |
| 6,010,586 A | 1/2000 | Suprise | |
| 6,018,822 A | 2/2000 | Hernandez | |
| 6,022,443 A | 2/2000 | Rajala et al. | |
| 6,098,557 A * | 8/2000 | Couillard et al. | 112/475.06 |
| 6,105,171 A | 8/2000 | Niedermeyer | |

| | | | | | |
|---|---|---|---|---|---|
| 6,142,983 A | 11/2000 | Suprise et al. | EP | 1 118 277 | 7/2001 |
| 6,145,132 A | 11/2000 | Towner | EP | 1 125 571 | 8/2001 |
| 6,149,637 A | 11/2000 | Allen et al. | EP | 1 159 883 | 12/2001 |
| 6,149,755 A | 11/2000 | McNichols et al. | EP | 1 166 730 | 1/2002 |
| 6,168,585 B1 | 1/2001 | Cesco-Cancian | EP | 1 179 302 | 2/2002 |
| 6,174,303 B1 | 1/2001 | Suprise et al. | EP | 1 184 012 | 3/2002 |
| 6,192,521 B1 | 2/2001 | Alberts et al. | EP | 1 188 427 | 3/2002 |
| 6,205,592 B1 | 3/2001 | Gouws | FR | 1276791 | 10/1960 |
| 6,248,097 B1 | 6/2001 | Beitz et al. | GB | 238557 | 8/1926 |
| 6,287,169 B1 | 9/2001 | Willms et al. | GB | 307652 | 3/1929 |
| 6,289,519 B1 | 9/2001 | Murakami et al. | GB | 571098 | 8/1945 |
| 6,293,934 B1 | 9/2001 | Kumasaka | GB | 620555 | 3/1949 |
| 6,293,936 B1 | 9/2001 | Otsubo | GB | 701081 | 12/1953 |
| 6,293,937 B2 | 9/2001 | Matsushita et al. | GB | 1342022 | 12/1973 |
| 6,308,339 B1 | 10/2001 | Murakami et al. | GB | 2069820 | 9/1981 |
| 6,312,420 B1 | 11/2001 | Sasaki et al. | GB | 2112268 | 7/1983 |
| 6,319,347 B1 | 11/2001 | Rajala et al. | GB | 2196525 | 5/1988 |
| 6,342,050 B1 | 1/2002 | Rönnberg et al. | GB | 2 208 263 | 3/1989 |
| 6,368,312 B1 | 4/2002 | Otsubo | GB | 2269978 | 3/1994 |
| D456,995 S | 5/2002 | Baker | GB | 2269998 | 3/1994 |
| 6,463,591 B1 | 10/2002 | Toratani | GB | 2269999 | 3/1994 |
| 6,475,201 B2 | 11/2002 | Saito et al. | GB | 2327859 | 2/1999 |
| 6,513,221 B2 | 2/2003 | Vogt et al. | JP | 04-242643 | 8/1992 |
| 6,516,473 B2 | 2/2003 | Saito | JP | 2000 093462 | 4/2000 |
| 6,539,554 B1 | 4/2003 | Portela | JP | 2000 355801 | 12/2000 |
| 6,560,786 B2 | 5/2003 | Lipton | JP | 2001 172801 | 6/2001 |
| 6,562,167 B2 | 5/2003 | Coenen et al. | JP | 2001 172802 | 6/2001 |
| 6,565,691 B2 | 5/2003 | Tomsovic et al. | JP | 3177341 | 6/2001 |
| 6,585,840 B2 | 7/2003 | Rabe et al. | JP | 2001 204762 | 7/2001 |
| 6,596,113 B2 | 7/2003 | Csida et al. | JP | 2001 204764 | 7/2001 |
| 6,610,901 B2 | 8/2003 | McMahon-Ayerst et al. | JP | 2001 204765 | 7/2001 |
| 6,626,883 B2 | 9/2003 | Wada et al. | JP | 3182069 | 7/2001 |
| 6,666,851 B2 | 12/2003 | Otsubo et al. | JP | 2001 207301 | 8/2001 |
| 6,723,034 B2 | 4/2004 | Durrance et al. | JP | 2001 224615 | 8/2001 |
| 6,807,685 B1 | 10/2004 | Hasegawa et al. | JP | 2001 238909 | 9/2001 |
| 2001/0014798 A1 | 8/2001 | Fernfors | JP | 2001 245929 | 9/2001 |
| 2001/0044614 A1 | 11/2001 | Damay et al. | JP | 2001 248002 | 9/2001 |
| 2002/0000291 A1 | 1/2002 | Coenen et al. | JP | 2001 254202 | 9/2001 |
| 2002/0002021 A1 | 1/2002 | May et al. | JP | 2001 262402 | 9/2001 |
| 2002/0002358 A1 | 1/2002 | Durrance et al. | JP | 3205643 | 9/2001 |
| 2002/0009940 A1 | 1/2002 | May et al. | JP | 3205690 | 9/2001 |
| 2002/0084017 A1 | 7/2002 | Rabe et al. | JP | 3208258 | 9/2001 |
| 2002/0087137 A1 | 7/2002 | Christoffel et al. | JP | 2001 299813 | 10/2001 |
| 2002/0092604 A1 * | 7/2002 | McCabe et al. ............ 156/202 | JP | 3221601 | 10/2001 |
| 2002/0099345 A1 | 7/2002 | Saito et al. | JP | 2001 309946 | 11/2001 |
| 2003/0109842 A1 | 6/2003 | Louis et al. | JP | 2001 333932 | 12/2001 |
| 2003/0115660 A1 | 6/2003 | Hopkins | JP | 2002 095700 | 4/2002 |
| 2004/0098791 A1 | 5/2004 | Faulks | JP | 2002-320641 | 11/2002 |
| 2004/0102746 A1 | 5/2004 | Mortell et al. | JP | 2004 159949 | 6/2004 |
| 2004/0107481 A1 | 6/2004 | Mortell et al. | WO | WO 95/16421 | 6/1995 |
| 2004/0116881 A1 | 6/2004 | Nordness et al. | WO | WO 95/18589 | 7/1995 |
| | | | WO | WO 96/03950 | 2/1996 |

FOREIGN PATENT DOCUMENTS

| | | |
|---|---|---|
| CA | 2356510 A1 | 2/2003 |
| DE | 435 579 | 2/1927 |
| DE | 809 844 | 8/1951 |
| DE | 839 244 | 5/1952 |
| DE | 101 44 255 | 2/2003 |
| EP | 0 217 032 | 4/1987 |
| EP | 0 585 766 | 3/1994 |
| EP | 0 717 971 | 6/1996 |
| EP | 0 763 353 | 3/1997 |
| EP | 0 549 988 | 6/1998 |
| EP | 0 904 758 | 3/1999 |
| EP | 0 911 006 | 4/1999 |
| EP | 0 925 729 | 6/1999 |
| EP | 0 933 072 | 8/1999 |
| EP | 1 048 231 | 11/2000 |
| EP | 1 060 677 | 12/2000 |
| EP | 1 060 679 | 12/2000 |
| EP | 1 108 371 | 6/2001 |
| EP | 1 108 372 | 6/2001 |
| EP | 1 108 373 | 6/2001 |
| EP | 1 110 463 | 6/2001 |

| | | |
|---|---|---|
| WO | WO 97/02797 | 1/1997 |
| WO | WO 99/33421 | 7/1999 |
| WO | WO 01/03524 | 1/2001 |
| WO | WO 01/58401 | 8/2001 |
| WO | WO 01/61093 | 8/2001 |
| WO | WO 01/67900 | 9/2001 |
| WO | WO 01/87217 | 11/2001 |
| WO | WO 01/87218 | 11/2001 |
| WO | WO 01/87562 | 11/2001 |
| WO | WO 01/87753 | 11/2001 |
| WO | WO 01/88245 | 11/2001 |
| WO | WO 02/49565 | 6/2002 |
| WO | WO 02/052967 | 7/2002 |
| WO | WO 03/041625 A1 | 5/2003 |
| WO | WO 03/057107 | 7/2003 |
| WO | WO 2004/062398 | 7/2004 |
| WO | WO 2004/073430 A2 | 9/2004 |

OTHER PUBLICATIONS

US 5,915,536, 06/1999, Alberts et al. (withdrawn)

* cited by examiner

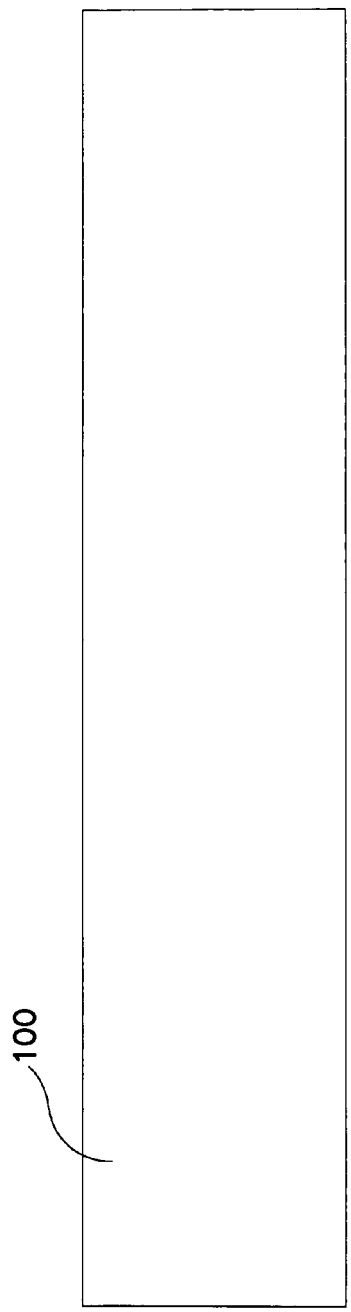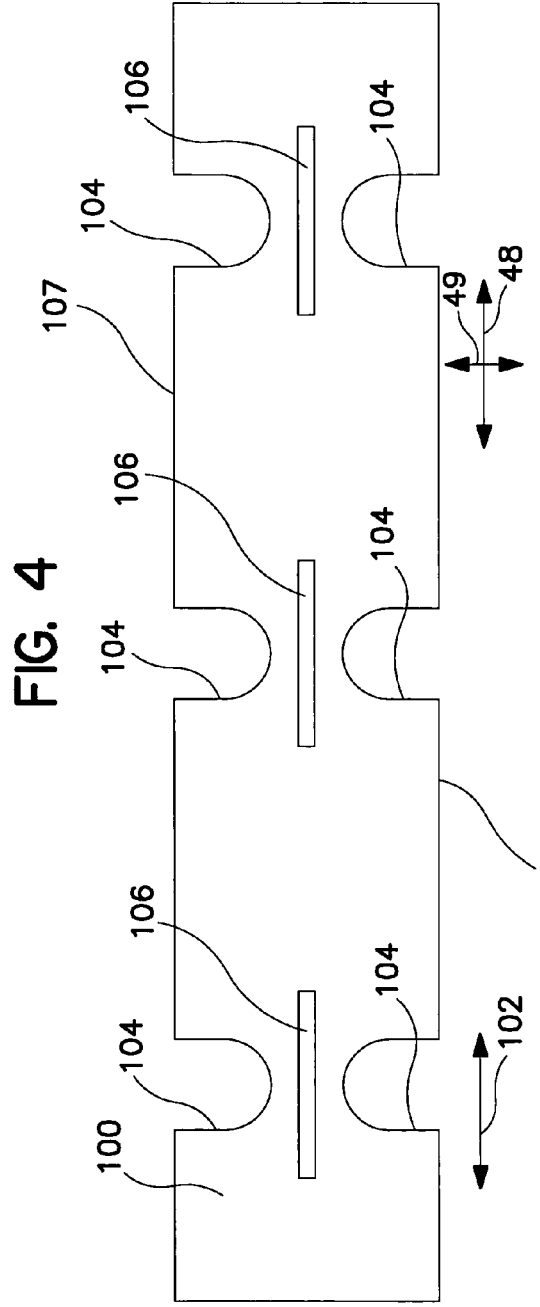

PROCESS OF MAKING BOXER SHORTS FROM A WEB

RELATED APPLICATION

This application is a continuation-in-part of U.S. patent application Ser. No. 10/314,915, filed Dec. 9, 2002. The disclosure of the prior application is incorporated herein by reference.

BACKGROUND OF THE INVENTION

This invention is directed to methods of making pants having side seams and a contracted crotch region. More particularly, the invention pertains to methods of making boxer shorts having side seams and a contracted crotch region. The boxer shorts may be absorbent or non-absorbent.

Pant-like garments have numerous applications including disposable clothing, training pants, feminine care products, adult incontinence products, disposable swimwear, or the like. Pant-like disposable garments are typically three-dimensional products with closed sides so that the product has a unitary waist opening and two leg openings. The wearer raises and lowers the garment to apply the product. Three-dimensional, boxer shorts-like products are particularly appealing because the boxer shorts look more like conventional articles of clothes.

Many disposable pants are formed as composite structures in which several components are combined to form a product specifically suited to its intended purpose. For example, disposable pants often include one or more absorbent materials intended to absorb various bodily exudates such as urine, menstrual fluid, and/or sweat. Such products may include a liquid permeable bodyside liner and a liquid impermeable outer cover, and can include other materials and features such as elastic materials and containment structures.

However, many disposable pants are aesthetically unappealing. Existing disposable absorbent pants can be overly bulky and often resemble disposable baby diapers. Various attempts have been made to provide disposable pants having an improved, more clothing-like appearance. However, disposable pants, particularly disposable absorbent boxer shorts, present many manufacturing challenges. In part, this is due to the high speed that is necessary to economically produce relatively low-cost disposable absorbent products. Product design is often compromised by cost and manufacturing constraints, resulting in disposable pants that lack aesthetic appeal and product function. In addition, crotch depth is required for a good fit, but difficult to achieve in a garment like boxer-shorts with hanging legs when using conventional manufacturing processes.

There is thus a need or desire for garment-like, aesthetically appealing boxer shorts, as well as methods of efficiently manufacturing such boxer shorts.

SUMMARY OF THE INVENTION

In response to the discussed difficulties and problems encountered in the prior art, new pants, and methods for manufacturing such pants, have been invented. The material for the garment shell of the pant is handled as a single web, or a continuous web of multiple pants, throughout assembly until seaming in order to streamline the assembly. The pants can include an absorbent assembly and can be made in either the machine direction or the cross direction.

One aspect of the invention pertains to a method of making a pant having side seams and hanging legs. One embodiment of the method comprises: providing a web; contracting the web in one or more selected areas; cutting at least one portion of the web to define leg openings; and attaching a first region and a second region together to form the side seams.

The web may be folded against a support structure. Examples of suitable support structures include internal support structures such as bars over which the web may be folded, or external support structures such as opposing vacuum conveyors between which the web may be folded. Additionally, the web may be contracted in the crotch region, or a strip applied to the crotch region, while the web is folded against the support structure. For instance, a strip may be applied to the web against the folded portion of the web while the web is on the support structure. The web may also be cut while on the support structure. In certain embodiments, a multi-lane production system may be used, in which case the web is folded against at least two support structures each parallel to a direction in which the web is conveyed, and each machine-direction array of pant assemblies is folded against a single support structure.

An absorbent structure may also be attached to the web. The absorbent structure may be attached to the web while the web is folded, prior to folding the web, or after unfolding the web.

The leg opening cut may result in a portion being removed along each of two transversely opposed edges of the web, or the leg openings may be formed from a slit along each of the transversely opposed edges of the web. The slit may be a single slit or a T-shaped slit. When a portion of the web is removed to form the leg openings, the cut portion may be either symmetrical or asymmetrical with respect to a transverse axis through the web. Examples of suitable symmetrical cuts include slots, such as single slots or T-shaped slots, U-shaped portions, mound-shaped portions, as well as teardrop or other shapes that are tapered at an open end of the leg openings. Examples of suitable asymmetrical cuts also include slots, teardrop or other shapes that are tapered at an open end of the leg openings, as well as cut portions that include at least one straight edge and at least one curvilinear edge. Any of the slits or cut portions may include a circular cut-out at the interior end of the leg opening to reduce the stress concentration.

Another aspect of the invention pertains to a pant made from a web. One embodiment of the pant comprises: a garment shell, the garment shell including a front region, a back region, and a contracted crotch region, side seams connecting the front region to the back region, and hanging legs. The pant may also include an absorbent structure. At least a portion of each of the front region, the back region, the contracted crotch region and the hanging legs include portions of the web.

The invention relates to a wide variety of absorbent and non-absorbent pants, including training pants, swim pants, diaper pants, incontinence garments, feminine care products, health care garments, apparel for institutional, industrial, and consumer use, or other garments. Disposable absorbent pants are adapted to be worn adjacent to the body of a wearer to absorb and contain various exudates discharged from the body.

BRIEF DESCRIPTION OF THE DRAWINGS

These and other objects and features of this invention will be better understood from the following detailed description taken in conjunction with the drawings, wherein:

FIG. 4 is a top view of a web.

FIG. 5 is a top view of the web of FIG. 4 including leg openings and strips applied to the web for assembling pants according to one embodiment of the invention using a machine direction assembly.

DEFINITIONS

Figure 1:
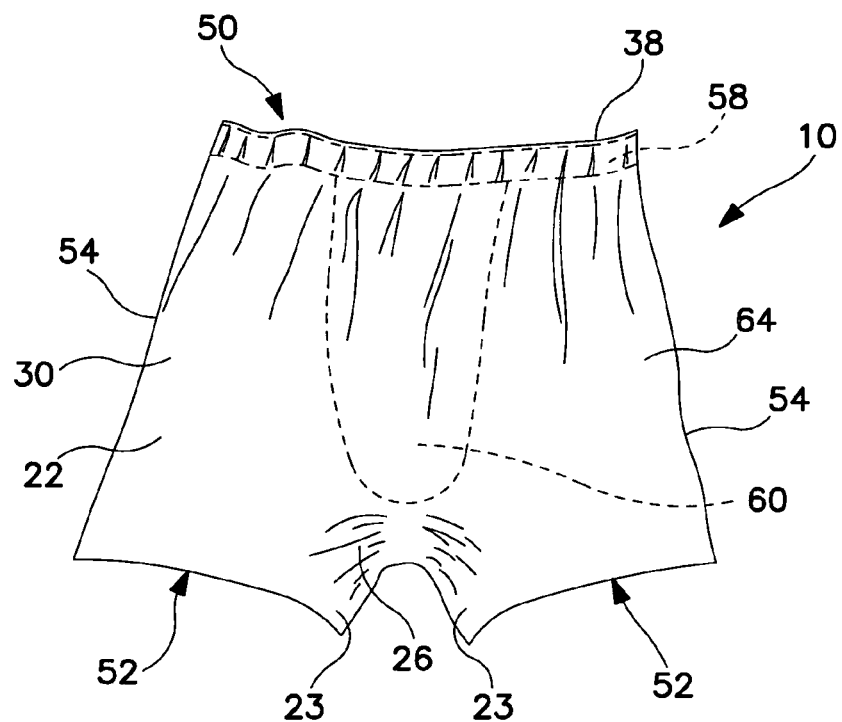
FIG. 1 is a front view of one embodiment of a pant according to the invention.

Within the context of this specification, each term or phrase below will include the following meaning or meanings.

"Attached" refers to the joining, adhering, connecting, bonding, or the like, of two elements. Two elements will be considered to be attached together when they are attached directly to one another or indirectly to one another, such as when each is directly attached to intermediate elements.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Boxer shorts" refers to a garment having hanging legs.

"Coform" is a composite material that is essentially an air-formed matrix of thermoplastic polymer microfibers, including meltblown fibers, and a multiplicity of individualized cellulose and/or staple fibers and/or particulates such as superabsorbents disposed throughout the matrix of microfibers and engaging at least some of the microfibers to space the microfibers to intertwine and hold captive within the matrix of microfibers by mechanical entanglement of the microfibers with the cellulose and/or staple fibers and/or particulates including superabsorbent.

"Comprising" is inclusive or open-ended and does not exclude additional, unrecited elements or method steps.

"Connected" refers to the joining, adhering, bonding, attaching, or the like, of two elements. Two elements will be considered to be connected together when they are connected directly to one another or indirectly to one another, such as when each is directly connected to intermediate elements.

"Corrugated" refers to the condition of a material which has been gathered into pleats or regular rugosities or folds, the material being shortened thereby.

"Cut-out" refers to a cut portion that includes one portion of a web removed from a remainder of the web, as opposed to a "slit," which is a cut in a web that does not result in the removal of any portion of the web.

"Disposable" refers to articles which are designed to be discarded after a limited use rather than being laundered or otherwise restored for reuse.

"Elastic," "elasticized," and "elasticity" mean that property of a material or composite by virtue of which it tends to recover its original size and shape after removal of a force causing a deformation.

"Elastomeric" refers to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Fabric" is used to refer to all woven, knitted and nonwoven fibrous webs.

"Flat web" comprises any material used for making garments that can be provided and processed in a substantially open, unfolded state; while the web can possess ripples or areas that do not lie exactly within an overall plane of the web, all points of the web should be reasonably identifiable as constituents in either an upper or a lower surface of the web. No portions of a flat web are enclosed or fixed into a loop or tunnel-like, or three-dimensional configuration.

"Garment shell" refers to an outer cover or outer layer of a garment. In a single-ply garment, the single layer of the garment is the garment shell.

"Garment insert" refers to an inner layer of a garment. The garment insert provides a close-to-the-body fit about a wearer's lower torso, thereby serving as a form of built-in underwear within the garment.

"Hanging legs" refers to the portions of a garment which extend from the crotch region downward to the leg openings. "Downward" refers to a direction toward the ground when the garment is positioned on a standing wearer.

"Hydrophilic" describes fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90 degrees are designated "wettable" or hydrophilic, while fibers having contact angles greater than 90 degrees are designated "nonwettable" or hydrophobic.

"Integral" is used to refer to various portions of a single unitary element rather than separate structures bonded to or placed with or placed near one another.

"Layer" when used in the singular can have the dual meaning of a single element or a plurality of elements.

"Liquid impermeable," when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

"Machine direction" refers to the length of a fabric in the direction in which it is produced, as opposed to "cross direction" which refers to the width of a fabric in a direction generally perpendicular to the machine direction.

Figure 10A:
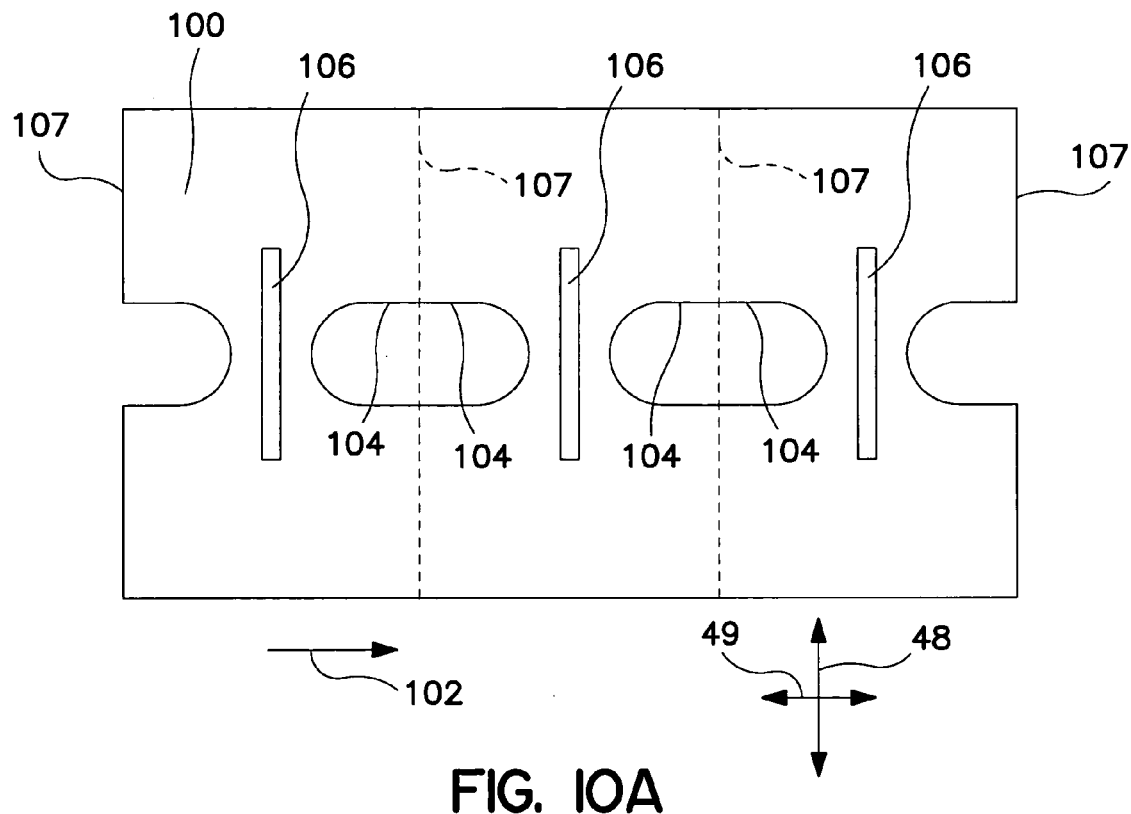
FIG. 10A is a top view of the web of FIG. 4 including leg openings and strips applied to the web for assembling pants according to one embodiment of the invention using a cross direction assembly.

The term "machine direction assembly" refers to a manufacturing process in which disposable products travel in an end-to-end or waist-to-waist orientation. A process utilizing a machine direction assembly entails products traveling in a machine direction through a converting machine with their longitudinal axes 48 (FIGS. 3A, 3C) parallel to the direction of arrow 102 (FIG. 5). "Cross direction assembly" entails the products traveling in a machine direction in a side-by-side orientation with their lateral axes 49 (FIGS. 3A, 3C) parallel to the direction of arrow 102, such as is illustrated in FIG. 10A.

"Member" when used in the singular can have the dual meaning of a single element or a plurality of elements.

"Nonwoven" and "nonwoven web" and "web" refer to materials and webs of material which are formed without the aid of a textile weaving or knitting process.

"Operatively joined," with reference to the attachment of an elastic member to another element, means that the elastic member can be attached to or connected to the element, and can additionally be treated with heat or chemicals, by pre-stretching, or the like, to give the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

The term "spunbonded fibers" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, U.S. Pat. No. 3,502,538 to Petersen, and U.S. Pat. No. 3,542,615 to Dobo et al. Spunbond fibers are quenched and generally not tacky on the surface when they enter the draw unit, or when they are deposited onto a collecting surface. Spunbond fibers are generally continuous and may have average diameters larger than 7 microns, often between about 10 and 30 microns.

"Stretchable" means that a material can be stretched, without breaking, by at least 50% (to 150% of its initial (unstretched) length) in at least one direction, suitably by at least 100% (to 200% of its initial length), desirably by at least 150% (to at least 250% of its initial length).

"Surface" includes any layer, film, woven, nonwoven, laminate, composite, or the like, whether pervious or impervious to air, gas, and/or liquids.

"Three-dimensional garment" refers to a garment that cannot be laid flat with all of its seams in one plane.

These terms may be defined with additional language in the remaining portions of the specification.

DESCRIPTION OF PREFERRED EMBODIMENTS

Figure 2A:
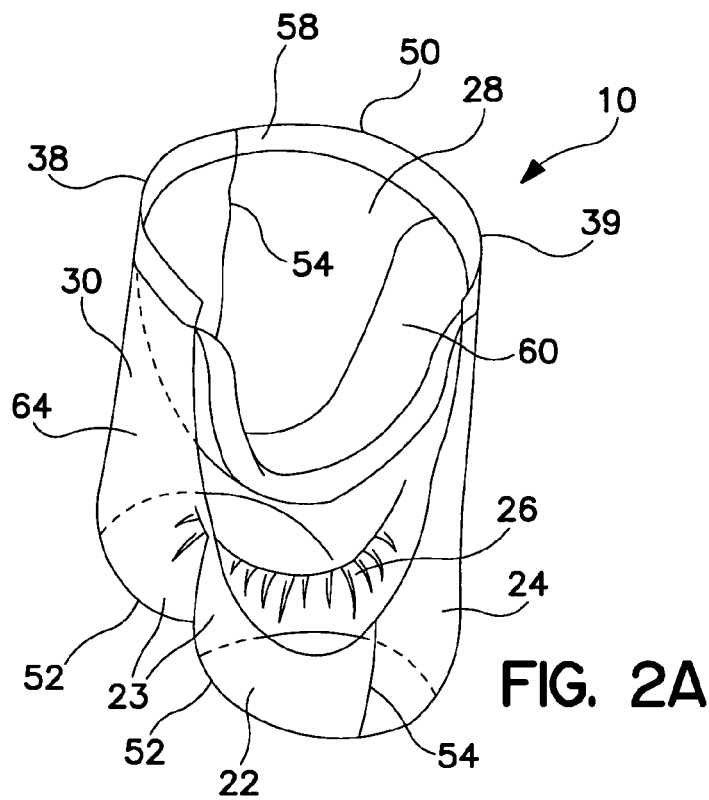
FIG. 2A is a perspective cut-away view of one embodiment of a pant according to the invention.
Figure 2B:
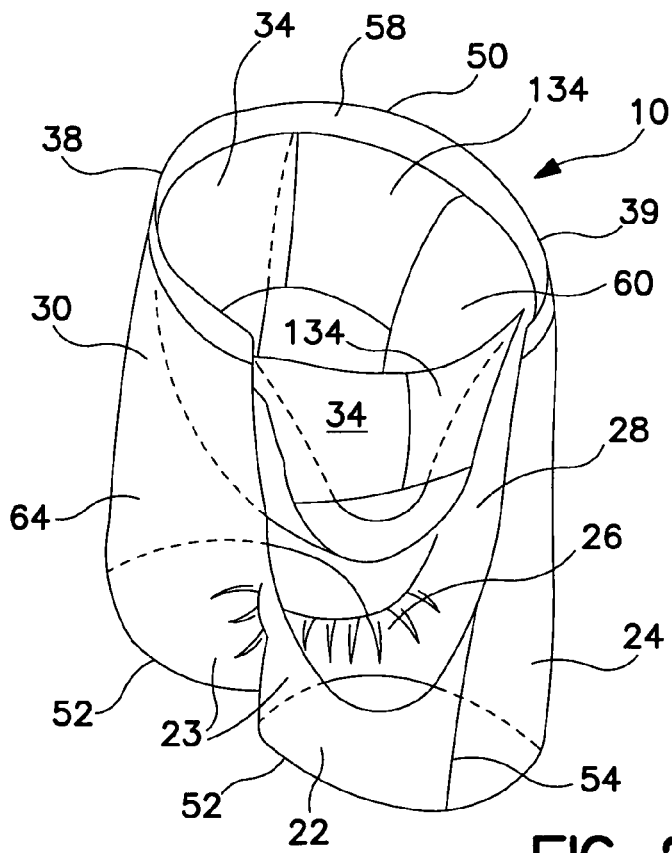
FIG. 2B is a perspective cut-away view of one embodiment of a pant according to the invention.

As representatively illustrated in FIGS. 1, 2A, and 2B, an embodiment of a pant 10 of the invention includes a garment shell 64. The garment shell 64 can include a front region 22, a back region 24, a contracted crotch region 26, an inner surface 28 which is configured to contact the wearer, and an outer surface 30 opposite the inner surface 28 which is configured to contact the wearer's clothing. The pant 10 also defines a pair of longitudinally opposed waist edges, which are designated front waist edge 38 and back waist edge 39. The front region 22 is contiguous with the front waist edge 38, and the back region 24 is contiguous with the back waist edge 39. The front region 22 includes the portion of the pant 10 which, when worn, is positioned on the front of the wearer while the back region 24 includes the portion of the pant 10 which, when worn, is positioned on the back of the wearer. The contracted crotch region 26 of the pant 10 includes the portion of the pant which, when worn, is positioned between the legs of the wearer and covers the lower torso of the wearer. As illustrated in FIGS. 1, 2A, and 2B the front and back regions 22 and 24 are joined together at side seams 54 to define a three-dimensional pant configuration having a waist opening 50 and a pair of leg openings 52. The contracted crotch region 26 may be positioned approximately transversely midway between the leg openings 52 and aligned with a longitudinal centerline of the garment shell 64. In particular embodiments, the pant 10 can include an absorbent structure 60.

The garment shell 64 includes a contracted crotch region 26. As described more fully below, the contraction of the contracted crotch region 26 can be accomplished either elastically or inelastically. The contraction of crotch region 26 provides crotch depth that provides a good fit through the contracted crotch region 26, thereby allowing the front and back regions to hang properly. The garment shell 64 can also include hanging legs 23 which extend from the contracted crotch region 26 downward to the leg openings 52 (FIGS. 1, 2A, and 2B).

The pant 10 also includes side seams 54 that connect the front region 22 to the back region 24 to create the pant 10. The side seams 54 can take any number of forms, including both refastenable and non-refastenable seams, as are known in the art. The provision of the side seams 54 can be accomplished in the manner described in U.S. Pat. No. 6,192,521 issued Feb. 27, 2001 to Alberts et al.; U.S. Pat. No. 5,046,272, issued Sep. 10, 1991 to Vogt et al., which is incorporated herein by reference, or in the manner described in U.S. Pat. No. 6,565, 691, issued May 20, 2003 to Tomsovic, et al.; U.S. Pat. No. 6,723,034 issued Apr. 20, 2004 to Durrance, et al.; U.S. Pat. No. 6,596,113 issued Jul. 22, 2003 to Csida, et al.; and/or U.S. Pat. No. 6,513,221 issued Feb. 4, 2003 to Vogt, et al.; all of which are incorporated herein by reference. As is known in the art, the side seams 54 can be inward or outward fin seams or lap seams (not shown).

The pant 10 can also have a waist elastic member 58 extending along at least a portion of the front waist edge 38 and/or the back waist edge 39. The waist elastic member 58 can be formed of any suitable elastic material. As is well known to those skilled in the art, suitable elastic materials include sheets, strands, or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic constrictive forces are imparted to the substrate. In one particular embodiment, for example, the waist elastic member 58 includes a plurality of dry-spun coalesced multifilament spandex elastomeric threads sold under the trade name LYCRA® and available from Invista Corporation, Wilmington, Del., U.S.A. Alternatively, multiple strands of 310 decitex LYCRA® may be also laminated at 250% elongation between spunbond facings in addition to an adhesive.

As another alternative, the waist elastic member 58 can be a material exhibiting delayed retraction, or can in fact be non-elastic. Delayed retraction materials may include those designed to retract relatively slowly following compression, such as "temporarily inhibited" elastic materials. "Temporarily inhibited" materials are described, for example, in U.S. Pat. No. 5,545,158 issued Aug. 13, 1996, to Jessup, U.S. Pat. No. 5,669,996 issued Sep. 23, 1997, to Jessup, and U.S. Pat. No. 5,500,063 issued Mar. 19, 1996, to Jessup, all of which are herein incorporated by reference, and references cited therein. Alternatively, a delayed retraction material may be designed to resist retraction until an activation process occurs, such as so-called "latent elastic" materials. Suitable retractive materials for use as a delayed retraction material can alternatively comprise any material adapted to retract upon activation, whether immediately upon activation or subsequently thereto. The retractive material may include elastomeric or nonelastomeric materials. Suitable nonelastomeric retractive materials may include without limitation polyether block amides (PEBAX®) or the like, and laminates thereof. Suitable elastomeric retractive materials may include without limitation LYCRA® materials, elastomeric materials including latex or rubber or synthetic urethanes, or the like, and laminates thereof. In particular embodiments, the retractive material may include an elastomeric material having an unstable state relative to some other stable and elastic state. In such embodiments, the retractive material can, but need not, have elastomeric properties in the unstable state. Other examples include heat-shrinkable elastic materials such as described in U.S. Pat. No. 4,816,094 issued Mar. 28, 1989 to Pomplun et al., U.S. Pat. No. 4,665,306 issued May 12, 1987 to Roland et al., and U.S. Pat. No. 4,663,106 issued May 5, 1987 to Pomplun et al., all of which are herein incorporated by reference.

A pant of this type can be designed to fit wearers in a wide range of sizes by adjusting the pant dimensions based on the anthropometric features of an intended wearer. Ratios of wearer dimensions to pant dimensions for a suitable boxer-style pant have been determined and are shown in Table 1. In addition, stylistic variations such as hip-hugging (low rise), relatively more closely or loosely fitted shorts, and other styles, may be provided by varying the ratios listed in Table 1 within (or even beyond) the ranges shown. Moreover, the use of elastomeric or extensible material to form the garment shell may provide additional adaptability to fit a wider range of wearer sizes.

Figure 1A:
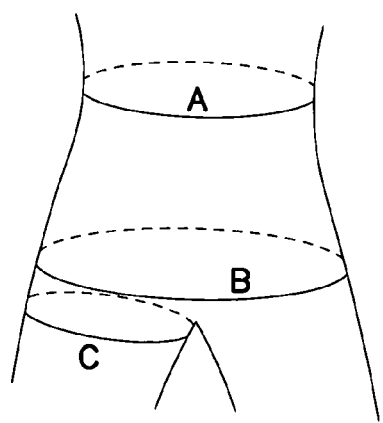
FIGS. 1A and 1B illustrate dimensions described with respect to Tables 1 and 2.
Figure 1B:
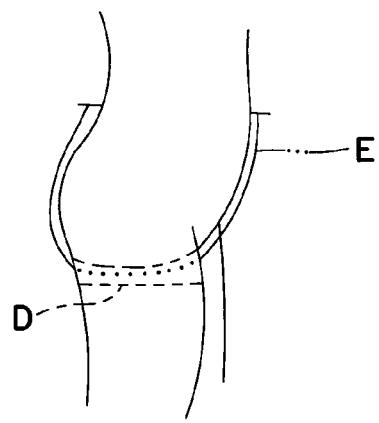

Since the pant dimensions are determined by the dimensions of the intended wearer, the ratios shown are based upon five measurements of an intended wearer, abbreviated as follows:

A: waist circumference (FIG. 1A)
B: hip circumference (FIG. 1A)
C: thigh circumference (measured in crotch region, horizontally; see FIG. 1A)
D: crotch depth (measured in crotch region, viewed 18 inches from the wearer's side; see FIG. 1B)
E: center front waist to center back waist through crotch; see FIG. 1B

Figures 5A, 5B:
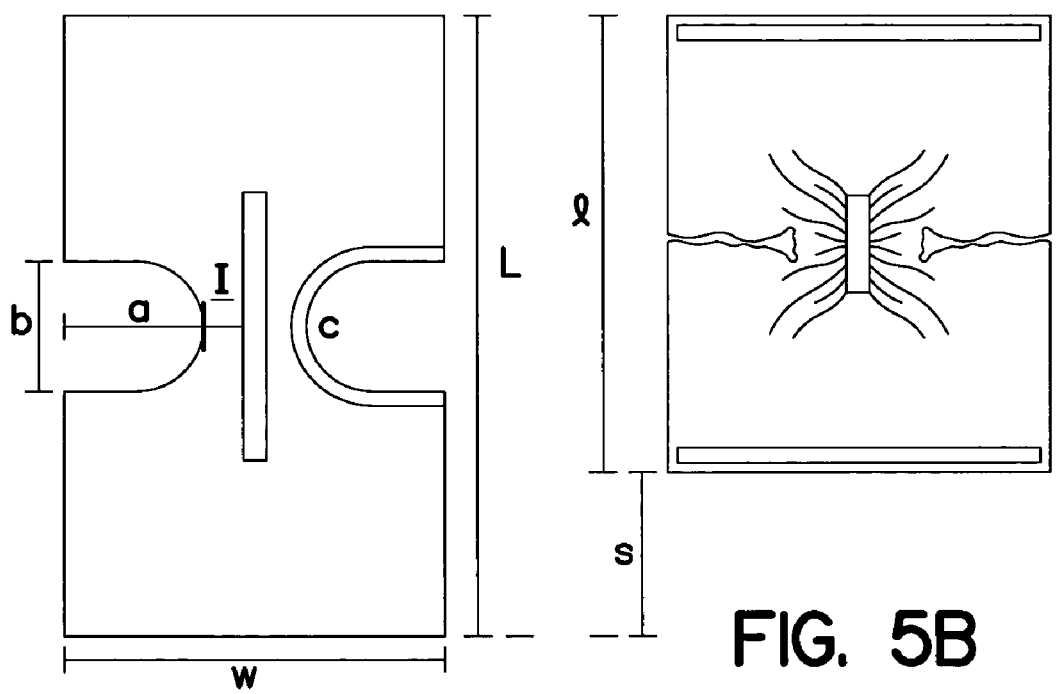
FIGS. 5A and 5B illustrate dimensions described with respect to Tables 1 and 2.

Table 2 shows how garment shell dimensions shown in FIGS. 5A and 5B are determined using body measurements A-E and ratios in Table 1. Table 2 also shows how the ratios in Table 1 have been applied to create shorts for two different size wearers, one a mannequin of a child (Wearer #1) weighing approximately 32 to 40 pounds (15-18 Kg), the other an adult female (Wearer #2) weighing approximately 125 pounds (57 Kg).

TABLE 1

| PANT DIMENSIONS | DETAILS and RATIOS | EXEMPLARY RANGES |
|---|---|---|
| Garment inseam I (FIG. 5A, dimension "I") | Selected based on garment style. There is not a seam at this location; this is simply the location where an "inseam" measurement is generally taken. After contraction, this dimension "I" provides the "hanging legs" feature of the pant. | 1-5 inches, or more |
| Width of garment shell (FIG. 5A, dimension "w") | Ratio of 2 × Width (i.e., garment circumference) to the larger of wearer's Hip or Waist circumference 2w:[B or A] | From about 1.2:1 to about 2:1, such as about 1.7, e.g. 2w = 1.2A or 1.2B |
| Length of base of arc (FIG. 5A, dimension "b") | Ratio of Arc base length to Wearer crotch depth b:D | From about 1:1 to about 1.5:1, such as about 1.25:1 |
| Circumference of leg opening (FIG. 5A, | Ratio of Leg opening to Wearer thigh circumference | From about 1.1:1 to about 1.5:1, such as about 1.25:1 |

TABLE 1-continued

| PANT DIMENSIONS | DETAILS and RATIOS | EXEMPLARY RANGES |
|---|---|---|
| dimension "c") Takeup (shortening) of garment shell on gathering of crotch (FIG. 5B, dimension "s") | c:C Ratio of Takeup to 2 × Garment inseam length I s:2I | From about 1:1 to about 1.6:1, such as about 1.3:1 |
| Length of garment shell after gathering (FIG. 5B, dimension "l") | Ratio of Length after gathering to Wearer F to B waist thru crotch l:E | This can vary widely depending on the desired short style, but for a standard fit, from about 1.1:1 to about 1.4:1, such as about 1.25:1, e.g. l = 1.4E |
| Length of garment shell before gathering (FIG. 5A, dimension "L") | Sum of Takeup and Length of shell after gathering s + l | |
| Arc height (FIG. 5A, dimension "a") | (Width of garment shell − 2 × Garment inseam I)/2 (w − 2I)/2 | |

TABLE 2

|   | Wearer #1 | Short #1 | Wearer #2 | Short #2 |
|---|---|---|---|---|
| A | 50 cm |  | 78 cm |  |
| B | 54 cm |  | 96 cm |  |
| C | 29 cm |  | 55 cm |  |
| D | 10 cm |  | 16.5 cm |  |
| E | 41 cm |  | 61 cm |  |
| I |  | 6 cm |  | 8 cm |
| w |  | 45 cm |  | 67 cm |
| b |  | 12.5 cm |  | 20.5 cm |
| c |  | 36 cm |  | 68 cm |
| s |  | 15.5 cm |  | 21 cm |
| l |  | 50.5 cm |  | 75 cm |
| L |  | 66 cm |  | 96 cm |
| a |  | 15 cm |  | 25 cm |

The pant 10 can also include an absorbent structure 60. The absorbent structure 60 can be attached to the garment shell 64 at the front waist edge 38 and back waist edge 39, or at some point below the front waist edge 38 and back waist edge 39 on the front region 22 and back region 24. (FIGS. 2A and 2B). Alternatively, the absorbent structure 60 can be attached to the garment shell 64 in the contracted crotch region 26. The absorbent structure 60 may be either permanently attached to the garment shell 64 or refastenably attached to the garment shell 64 to allow for replacement of absorbent structures 60 when the absorbent structures 60 become soiled.

The absorbent structure 60 can be any structure that is generally compressible, conformable, non-irritating to the skin, and capable of absorbing and retaining liquids and certain body wastes. The absorbent structure 60 can be manufactured in a wide variety of sizes and shapes, from a wide variety of liquid absorbent materials commonly used in the art, and may be stretchable, non-stretchable, or elastic. For example, the absorbent structure 60 can suitably include a matrix of hydrophilic fibers, such as a web of cellulosic fluff, mixed with particles of a high-absorbency material commonly known as superabsorbent material. In a particular embodiment, the absorbent structure 60 includes a matrix of cellulosic fluff, such as wood pulp fluff, and superabsorbent hydrogel-forming particles. The wood pulp fluff can be exchanged with synthetic, polymeric, meltblown fibers or short cut homofil bicomponent synthetic fibers and natural fibers. The superabsorbent particles can be substantially homogeneously mixed with the hydrophilic fibers or can be nonuniformly mixed. The fluff and superabsorbent particles can also be selectively placed into desired zones of the absorbent structure 60 to better contain and absorb body exudates.

The concentration of the superabsorbent particles can also vary through the thickness of the absorbent structure 60. Alternatively, the absorbent structure 60 can include a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers, for example, sodium neutralized polyacrylic acid. Suitable superabsorbent materials are available from various commercial vendors, such as Dow Chemical Company located in Midland, Mich., U.S.A., and Stockhausen, Inc. in Greensboro, N.C., U.S.A. Typically, a superabsorbent material is capable of absorbing at least about 15 times its weight in water, and desirably is capable of absorbing more than about 25 times its weight in water.

In one embodiment, the absorbent structure 60 includes a blend of wood pulp fluff and superabsorbent material. One preferred type of pulp is identified with the trade designation CR1654, available from U.S. Alliance, Childersburg, Ala., U.S.A., and is a bleached, highly absorbent sulfate wood pulp containing primarily soft wood fibers and about 16 percent hardwood fibers. As a general rule, the superabsorbent material is present in the absorbent structure 60 in an amount of from 0 to about 90 weight percent based on total weight of the absorbent assembly. The absorbent structure 60 suitably has a density within the range of about 0.10 to about 0.35 grams per cubic centimeter. The absorbent structure 60 may or may not be wrapped or encompassed by a suitable tissue or nonwoven wrap that may help maintain the integrity and/or shape of the absorbent assembly.

The absorbent structure 60 can also incorporate other materials that are designed primarily to receive, temporarily store, and/or transport liquid along the mutually facing surface with absorbent structure 60, thereby maximizing the absorbent capacity of the absorbent assembly. One suitable material is referred to as a surge layer (not shown) and includes a material having a basis weight of about 50 to about 120 grams per square meter, and including a through-air-bonded-carded web of a homogenous blend of 60 percent 3 denier type T-256 bicomponent fiber including a polyester core/polyethylene sheath and 40 percent 6 denier type T-295 polyester fiber, both commercially available from Kosa Corporation of Salisbury, N.C., U.S.A.

In particular embodiments, the absorbent structure 60 is thin to provide a slim, comfortable, non-bulky pant 10. Any suitable thin absorbent structure may be used, such as for example, the thin absorbent described in WO 02/49565, published Jun. 27, 2002, by Sawyer et al., which is incorporated herein by reference.

The absorbent structure 60 can include a pair of containment flaps 62 (FIG. 3A) which are configured to provide a barrier to the transverse flow of body exudates. A flap elastic member (not shown) can be operatively joined with each containment flap 62 in any suitable manner as is well known in the art. The elasticized containment flaps 62 define an unattached edge which assumes an upright, generally perpendicular configuration to form a seal against the wearer's body. Suitable constructions and arrangements for the containment flaps 62 are generally well known to those skilled in the art and are described in U.S. Pat. No. 4,704,116 issued Nov. 3, 1987, to Enloe, which is incorporated herein by reference.

As an alternative, a pant-like garment insert could be used for the absorbent structure 60. For example, the pant-like garment insert may include a body side liner, an outer cover, and an absorbent assembly between the body side liner and the outer cover, and side panels. Examples of suitable pant-like garment inserts include a training pant, such as HUGGIES® PULL-UPS® Disposable Training Pants, or a disposable underpant, such as GOODNITES® Disposable Underpants, both manufactured by Kimberly-Clark Corporation, Neenah, Wis., U.S.A. A training pant serving as the pant-like garment insert for the absorbent structure 60 can include front side panels 34 and back side panels 134 (FIGS. 2B and 3B). The manufacture of training pants having side panels can be accomplished in the manner described in U.S. Pat. No. 6,562,167, issued May 13, 2003 to Coenen et al., which is incorporated herein by reference.

As another alternative, a pad-type absorbent could be used for the absorbent structure. The pad-type absorbent can be attached in the crotch region 26 of the pant 10. An example of a suitable pad-type absorbent is a feminine care pad such as KOTEX® Feminine Napkins, KOTEX® LIGHTDAYS® disposable panty liners, or an incontinence absorbent pad such as POISE® Feminine Guards and Pads or DEPEND® Guards for Men, all manufactured by Kimberly-Clark Corporation, Neenah, Wis., U.S.A.

Figure 3A:
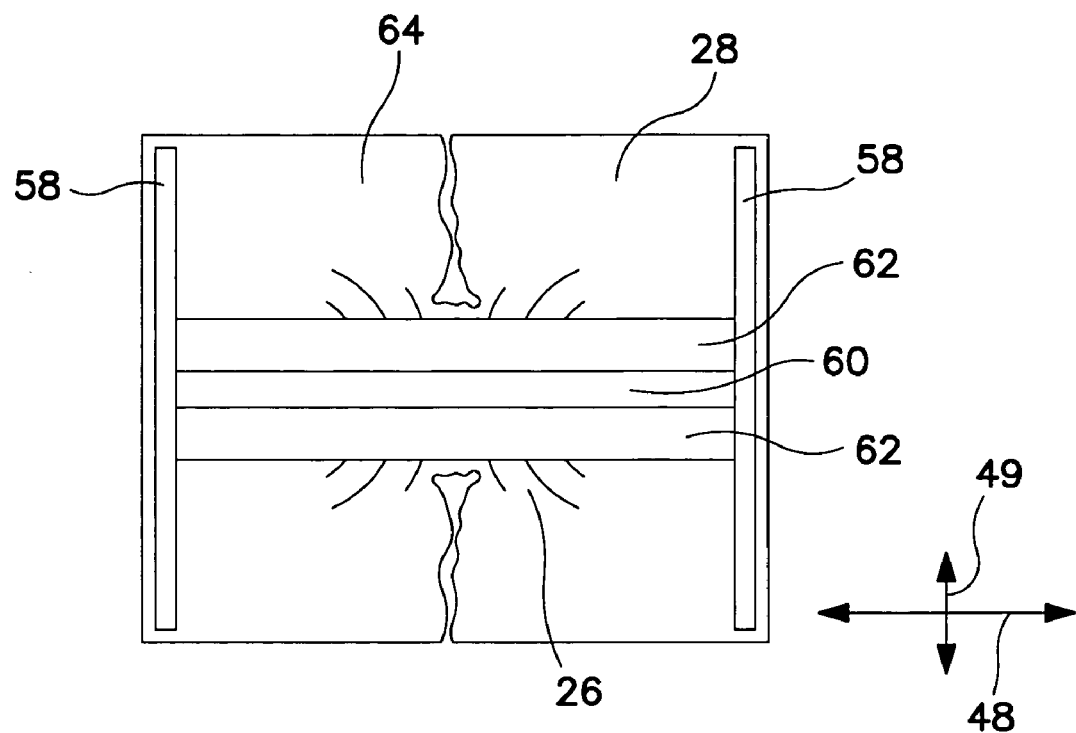
FIG. 3A is a plan view of the garment shown in FIG. 2A, showing the side facing the wearer.
Figure 3B:
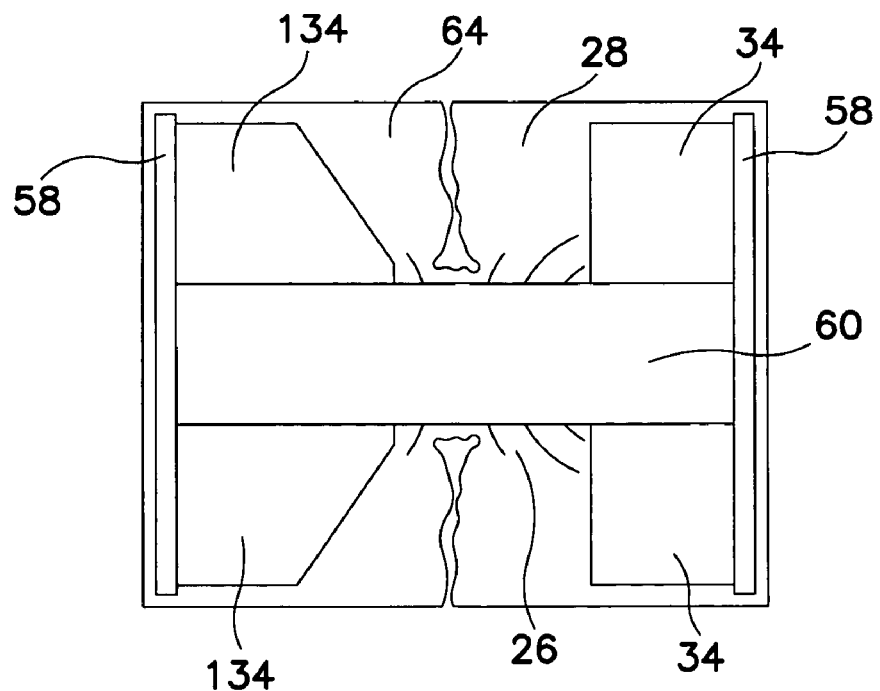
FIG. 3B is a plan view of the garment shown in FIG. 2B, showing the side facing the wearer.
Figure 3C:
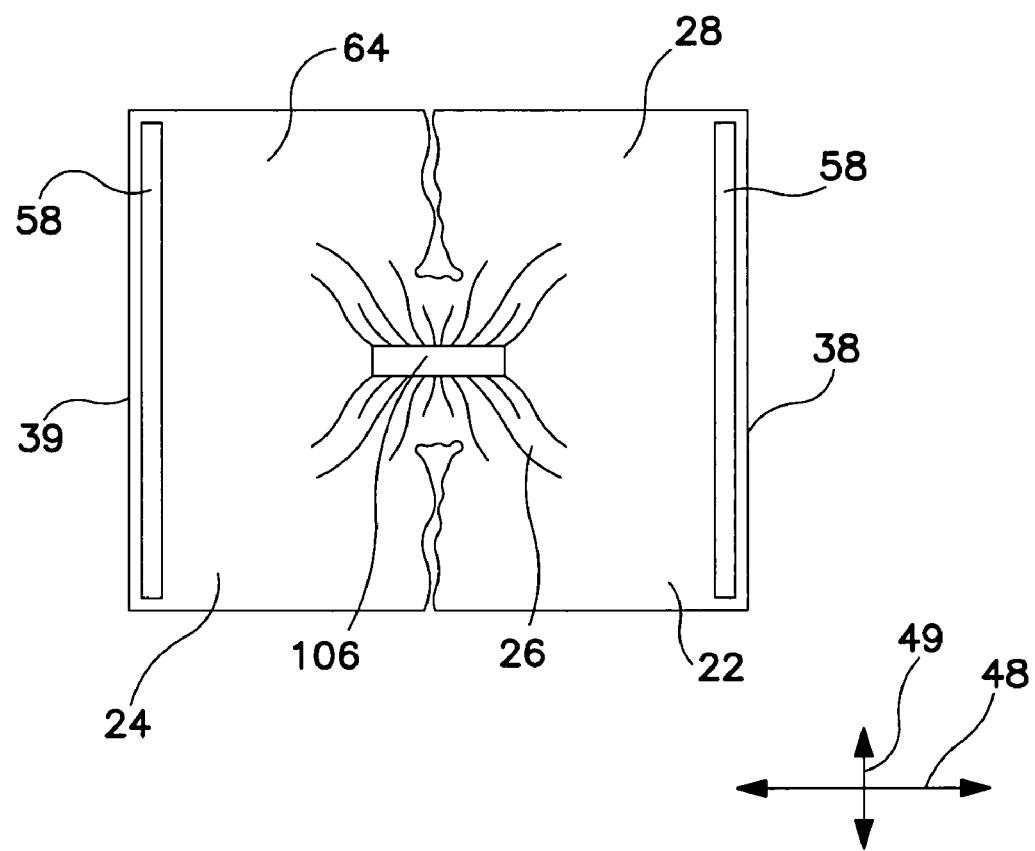
FIG. 3C is a plan view of the garment shown in FIG. 2A, showing the side facing the wearer without an absorbent structure.

For reference, arrows 48 and 49 depicting the orientation of the longitudinal axis and the transverse axis, respectively, of the garment shell 64 are illustrated in FIGS. 3A, 3C, and 5.

The garment shell 64 is suitably constructed of materials that are comfortable against the skin and non-irritating. It is contemplated that the garment shell 64 can be either disposable or durable. Both nonwoven and woven materials are contemplated for the garment shell 64. For example, the garment shell 64 for pant 10 can be selected from a wide variety of materials, including elastic, stretchable, or nonstretchable materials. The garment shell 64 can be a single layer of material or a multi-layered laminate structure. One example of a suitable material is a spunbond polypropylene nonwoven web. The garment shell 64 itself may be absorbent and, for example, may be made of those materials of which the absorbent structure 60 is made. For instance, the garment shell 64 may include a coform material with a polyethylene film on an outer surface of the garment. The garment shell 64 suitably provides a relatively cloth-like texture to the wearer.

The present invention also includes various methods for making pants from a web. Referring to FIG. 4, a single web 100 is provided moving in the direction represented by arrow 102. Alternatively, two webs that are joined at their edges to form a double-width piece (not shown) can be used for the web 100. The web 100 may be a flat web and can be composed of any material previously described for the garment shell 64.

The method can be carried out using machine direction assembly so that arrow 102 can correspond to the longitudinal direction parallel to the longitudinal axis 48 as shown in FIG. 5 with the products connected end-to-end or waist-to-waist, or the method can be carried out using cross direction assembly so that arrow 102 can correspond to the transverse direction parallel to the transverse axis 49 as shown in FIG. 10A with the products connected side-to-side.

In both the machine direction process (FIGS. 5-9) and the cross direction process (FIGS. 10A-12), the web 100 is cut along each of the transversely opposed edges 107 of the web 100 to define leg openings 104 (FIGS. 5 and 10A). More particularly, the leg opening 104 may be formed by slitting or die-cutting or otherwise removing a portion of the web 100 from the remainder of the web 100. The geometry of the leg opening 104 affects the overall product appearance. Examples of suitable cuts for creating leg openings 104 are illustrated in FIGS. 13A-13L.

When in a flat configuration, as illustrated in FIGS. 13A-13L, the leg openings 104 may simply be slits (FIGS. 13A-C) within the web, or either symmetrical (FIGS. 13D-I) or asymmetrical (FIGS. 13J-L) portions cut and removed from along each of the transversely opposed edges 107 of the web. Any suitable symmetrical or asymmetrical shape may be cut to form the leg openings 104. As referred to herein, the symmetry of the leg opening cut-outs is determined with respect to a transverse axis 49 through the web. Alternatively, the leg openings 104 may be formed by folding material adjacent to a slit in order to move a portion of the material out of the way.

Figure 13A:
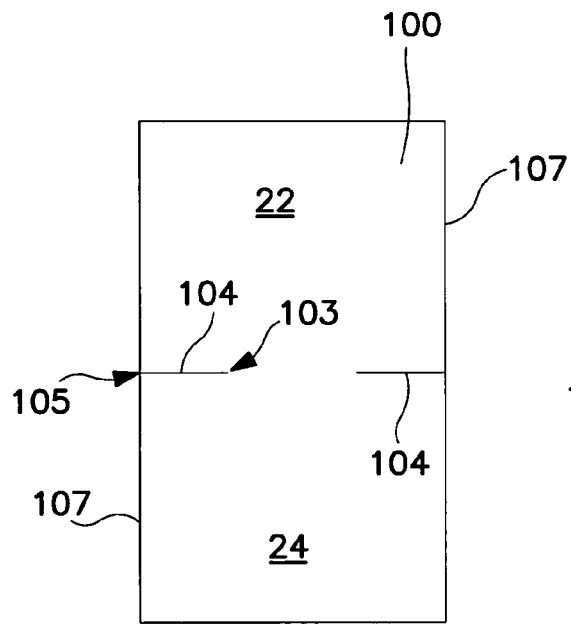
FIGS. 13A-13L are top views of the web having various leg opening embodiments.
Figure 13B:
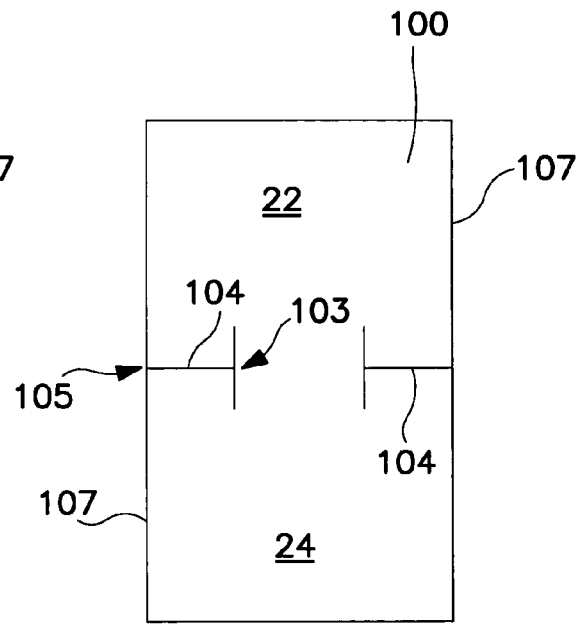

As illustrated in FIG. 13A, the leg openings 104 may be formed from single slits. Slits can result in longer legs in the garment compared to leg openings created from portions of the web that are cut out and removed from the remainder of the web. Alternatively, the leg openings 104 may be formed from T-shaped slits, as shown in FIG. 13B. Expanding the interior end 103 of the slits into a "T" shape provides pant legs that hang smoothly adjacent to the crotch region 26. Additionally, the portion of the slit extending from the interior end 103 to an open end 105 of the T-shaped slit may be hemmed along one or both edges forming this portion of the slit. Similarly, in embodiments other than T-shaped slits, a portion of the web adjacent to the cut may be folded and manipulated out of the way to create a larger leg opening 104.

Figure 13C:
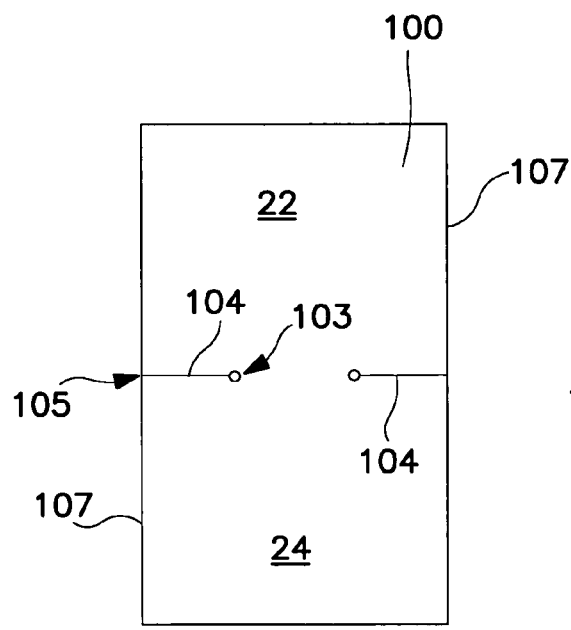

Slits may be cut using pinch-cut knives, intermittent slitters, or any other suitable straight machine-direction or cross-direction cut. Not only do the slits result in longer legs on the garment, but less Web 100 material waste accrues than in the cut-out embodiments. The slits may be reinforced or otherwise adapted at the shaped interior ends 103 of the leg openings, as shown in FIG. 13C and described in further detail below. As another alternative, the slits need not initially extend all the way to the transverse edges 107 of the web, but instead may be cut within the web for easier handling of the web during the pant-forming process, and may or may not be cut at the transverse edges 107 of the web later during the pant-forming process.

Figure 13D:
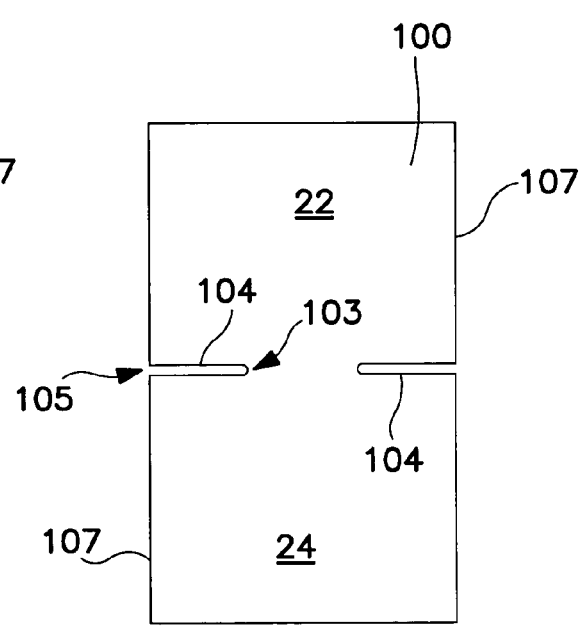
Figure 13E:
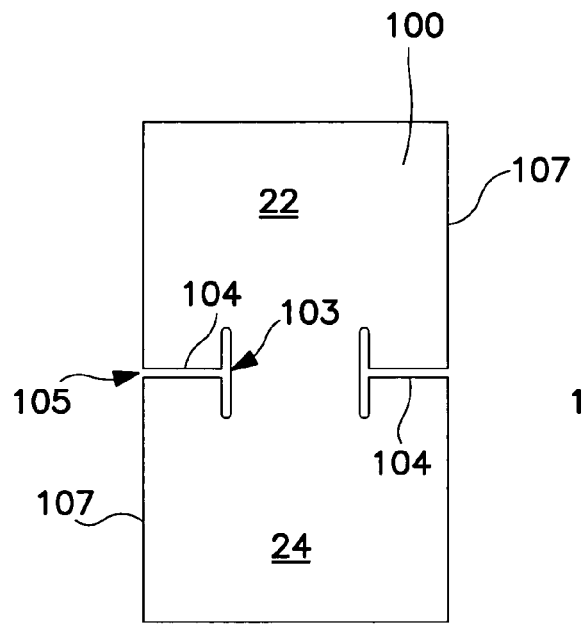
Figure 13F:
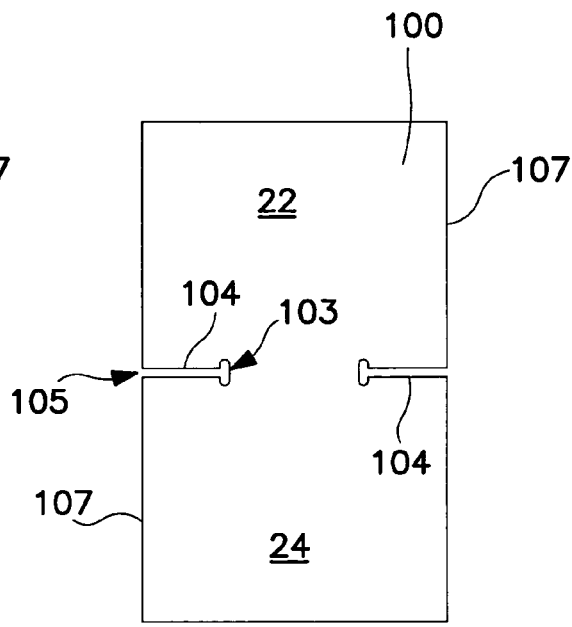

Alternatively, rather than slits, the leg openings 104 may be formed from slots, which as used herein refers to cut-outs that resemble the shape of slits but with at least some portion of the web 100 removed from the remainder of the web. The slots may be symmetrical, as illustrated in FIGS. 13D-F, or asymmetrical, as illustrated in FIG. 13J. More particularly, the slots may form substantially straight lines, as shown in FIGS. 13D and 13J, or T-shaped slots, as shown in FIG. 13E, or a slot having a reinforced interior end 103 resembling a hairpin shape, as shown in FIG. 13F.

Figure 13G:
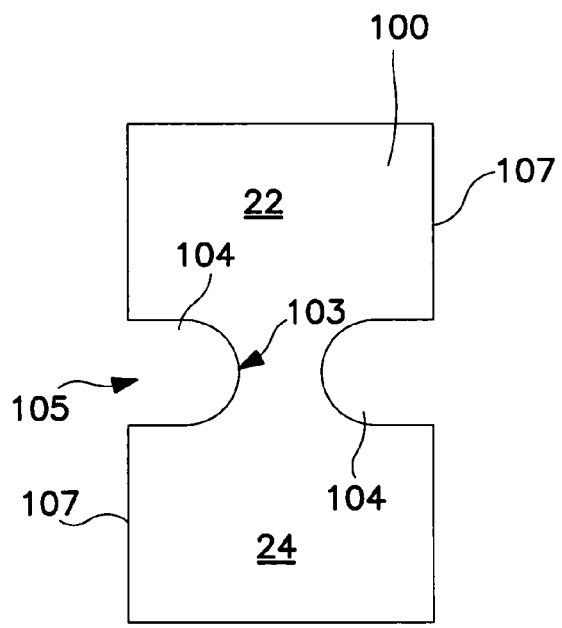
Figure 13H:
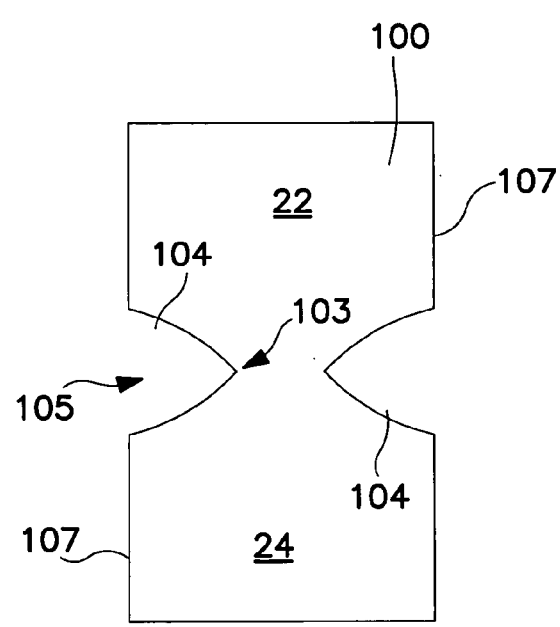

Other suitable symmetrical shapes that may be cut and removed from the web 100 to form the leg openings 104 include a "U" shape, as illustrated in FIG. 13G, as well as a "mound" shape, as illustrated in FIG. 13H. The U-shaped leg opening 104 results in relatively short garments legs, whereas mound-shaped leg openings 104 may provide more body coverage than the U-shaped leg openings 104. The term "mound-shaped" refers to a cut-out portion having an angle at the interior end 103 that is less than 180 degrees, thereby resulting in a leg opening 104 having a triangular shape, or a softened triangular shape that may resemble the shape of a mound or a mountain.

Figure 6:
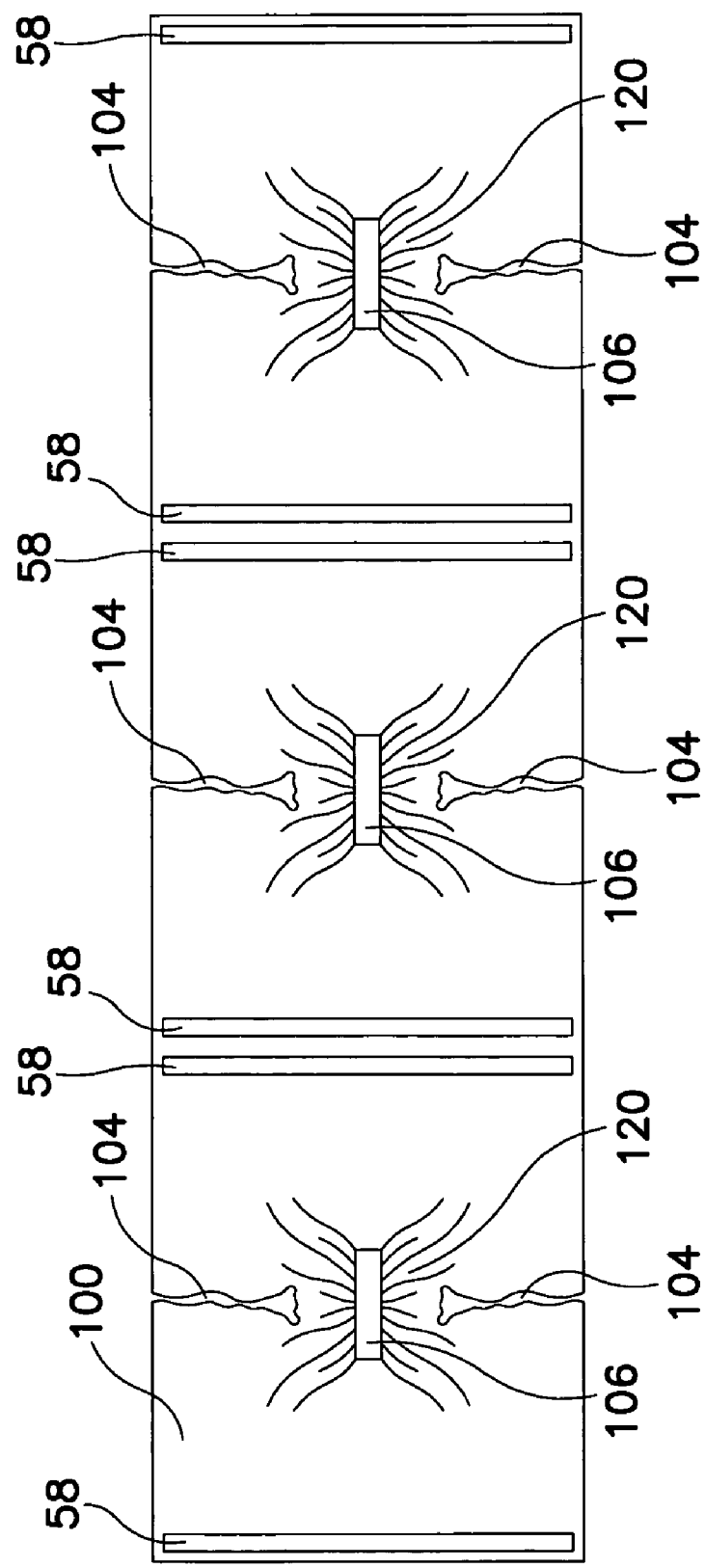
FIG. 6 is a top view of the web of FIG. 5 after contraction of the web.
Figure 11:
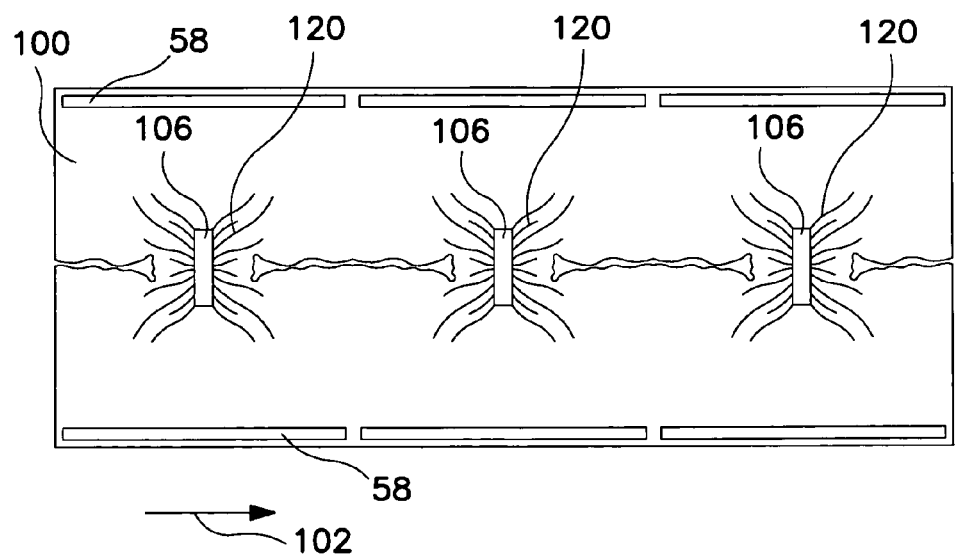
FIG. 11 is a top view of the web of FIG. 10A after contraction of the web.
Figure 13I:
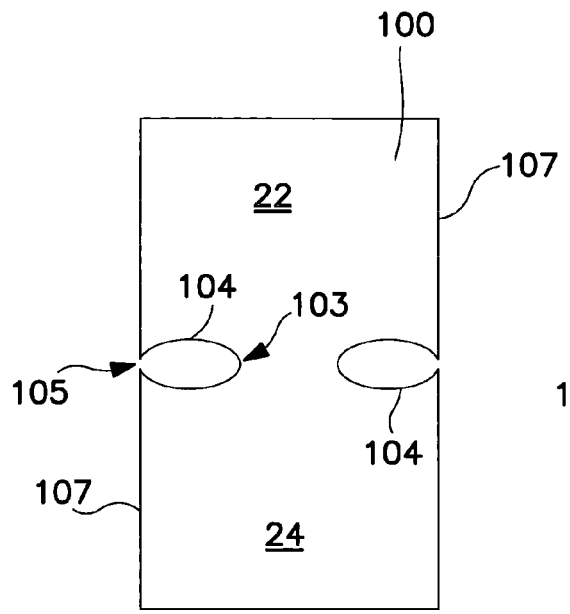
Figure 13J:
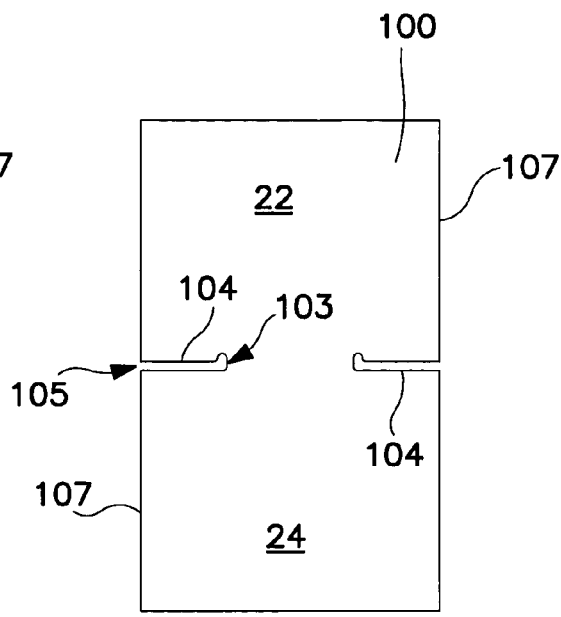
Figure 13K:
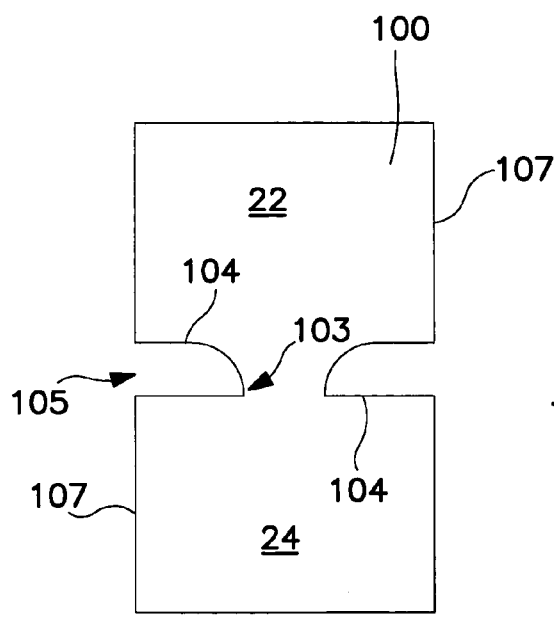
Figure 13L:
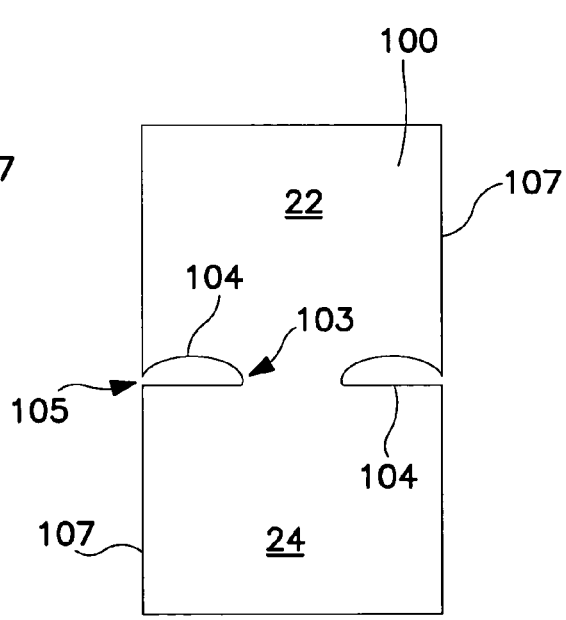

Rather than expanding from the interior end 103 of the leg opening 104 to the open end 105 of the leg opening, the leg openings 104 may be tapered at the open ends 105, thereby resulting in a teardrop shape. The tapered shape can provide a straight horizontal appearance along the leg ends of the garment even though the contracted area 120 (as shown in FIGS. 6 and 11) distorts the lower region of the garment. The tapered shape may be either symmetrical, as illustrated in FIG. 13I, or asymmetrical, as illustrated in FIG. 13L.

As an alternative to slits and/or symmetrical cut-outs, the leg openings 104 may be any suitable asymmetrical shape. For example, as shown in FIG. 13K, the leg openings 104 may include a straight edge along a front edge of the cut-out and a curvilinear edge along a back edge of the cut-out. This asymmetrical design may provide greater butt coverage in the back of the garment and longer legs in the front of the garment.

Many of the shapes of the leg openings 104 may be adapted for reinforcement by cutting a circular cut-out at the interior end 103 of the leg openings 104 to reduce stress concentration at the interior end of the openings, thereby reducing the likelihood of tearing in the crotch region 26. An example of this type of reinforcing cut-out is illustrated in FIG. 13C. The reinforcing cut-out may be other suitable shapes besides circular. For example, when the leg openings 104 are formed from slots, the reinforcing cut-out may have a shape that is wider than the longitudinal opening of the slot and narrower than the transverse opening of the slot to reduce the stress concentration. A suitable shape may be circular or oblong, as illustrated in FIG. 13F.

As more fully described below, the leg openings 104 become the leg openings 52 of the pant 10.

In the machine direction process (FIGS. 5 and 6-9), strips 106 may be applied to selected areas located between the leg openings 104. Strips 106 can include elastic or non-elastic material. Examples of suitable non-elastic material include heat contractible materials, such as heat shrinkable films, for example, films formed of polyether block amides (PEBAX®, available from the Atofina Company of France) or the like. If the strips 106 are elastic, the elastic can be formed of any suitable material previously described for the waist elastic member 58. As an alternative, strips 106 can include any of the previously described delayed retraction materials.

Figure 7:
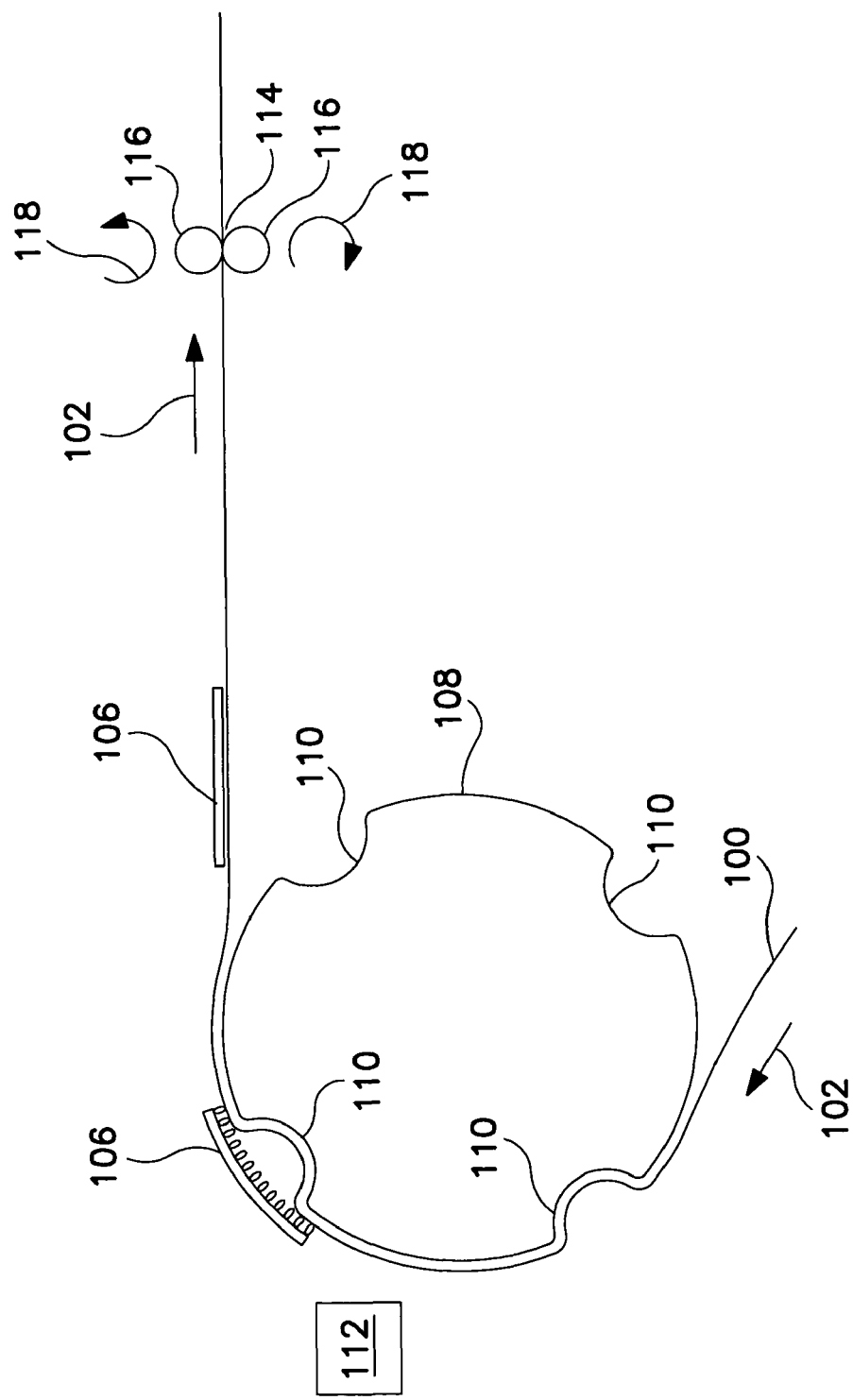
FIG. 7 is a side view of a looper drum for applying an elastic strip to the web.

Referring to FIG. 7, if the strips 106 are elastic, the strips 106 can be applied to the web 100 using a looper drum 108. Looper drums like looper drum 108 are known and are described, for example, in U.S. Pat. No. 5,171,388 issued Dec. 15, 1992 to Hoffman et al., herein incorporated by reference. Drum 108 includes surface grooves 110. Drum 108, as illustrated in FIG. 7, includes four surface grooves 110, but any number of surface grooves 110 may be included. The surface grooves 110 are spaced around the drum 108 so that each garment shell 64 eventually includes one strip 106.

The web 100 travels around the drum 108 in the direction of arrow 102. The web 100 runs down into the surface grooves 110 by virtue of the fact that the drum 108 includes apertures across its surface and is under vacuum. Adhesive (shown for purposes of illustration as dots between strip 106 and the web 100 over the surface groove 110) can be applied to the strip 106. Alternatively, the adhesive can be applied to the web 100 in the selected areas between leg openings 104. Suitable adhesives, which can be applied continuously or intermittently as beads, a spray, parallel swirls, or the like, can be obtained from Bostik Findley Adhesives, Inc., of Wauwatosa, Wis., U.S.A., or from National Starch and Chemical Company, Bridgewater, N.J. U.S.A.

The web 100 passes by the elastic application module 112 and the strip 106 of elastic is applied in a substantially unstretched condition to the web 100 over the surface groove 110. The web 100 with the strip 106 of elastic continues moving in the direction of arrow 102 out of surface groove 110 and off the drum 108. The web 100 with strip 106 of elastic passes through nip 114 to press and secure the strip 106 of elastic to the web 100. The nip 114 is defined by rolls 116 turning in the direction of arrows 118. In the alternative, any other suitable method for pressing and securing the strip 106 of elastic to the web 100 can be used. As web 100 exits the nip 114, the web 100 can be drawn at a slower rate by the downstream process than the surface speed of rolls 116, allowing the strip 106 of elastic to contract and reduce the length of web 100.

FIG. 6 shows the web 100 after the contraction of the strips 106. The contraction of the web 100 defines contracted areas 120 in the selected areas between leg openings 104. The contracted area 120, as described more fully below, becomes the contracted crotch region 26 of the pant 10.

Alternatively, the strip 106 can be applied to the web 100 by any other method known in the art such as, for example, a corrugating drum such as that described in U.S. Pat. No. 4,397,704 issued Aug. 9, 1983 to Frick, or an elastic application system in which the material is gathered into folds running in the cross direction and a continuous elastic is applied in the machine direction and severed at the location of the folds in the base material such as described in U.S. Pat. No. 4,417,938 issued Nov. 29, 1983 to Sigl, or an intermittent adhesive application that allows the elastic to snap back from non-adhesive zones, a high efficiency interface roll such as that described in U.S. Pat. No. 6,022,443 issued Feb. 8, 2000 to Rajala et al., U.S. Pat. No. 5,556,504 issued Sep. 17, 1996 to Rajala et al., and U.S. Pat. No. 6,319,347 issued Nov. 20, 2001 to Rajala et al., all of which are here incorporated by reference, or by any other any means known in the art.

FIGS. 6 and 11 also show waist elastics 58 applied to the web 100. The waist elastics 58 can be applied by any method known in the art at any stage in the manufacturing of the pant 10.

As an alternative, the tension on the web 100 can be reduced by cutting the web 100 into separate pieces approximately midway between successive strips 106 to define a garment shell 64 (FIG. 3C). It is also contemplated, however, that the step of cutting the web 100 can be carried out after contraction of the web 100. It is further contemplated that, instead of a continuous web of multiple garment assemblies connected to one another, the web 100 may exist as a single garment assembly or garment shell 64 at the outset of the process. This option exists in both the machine direction process as well as the cross direction process.

Figure 8A:
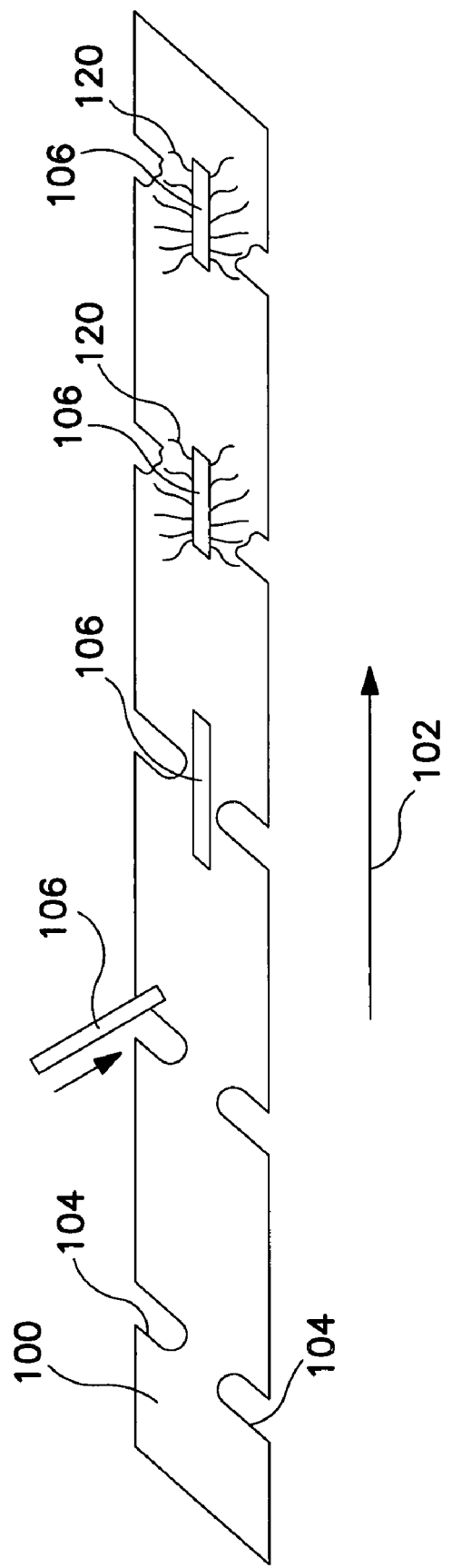
FIG. 8A is a side view of a process for applying a strip to the web.

Referring to FIG. 8A, the strips 106, whether elastic or nonelastic, can be applied to the selected areas of the web 100 between the leg openings 104 by a cut-and-place module (not shown) as is commonly known in the art.

Next, the web 100 can be contracted elastically or inelastically by any suitable means. For example, if the strip 106 is an elastic capable of delayed retraction, the web 100 can be contracted by activating the strip 106 to restore the elasticity by time, temperature, radiation or other appropriate energy. If the strip 106 is a heat shrinkable material, the web 100 can be contracted inelastically by activating the heat shrinkable material by applying heat or other appropriate energy.

Figure 8B:
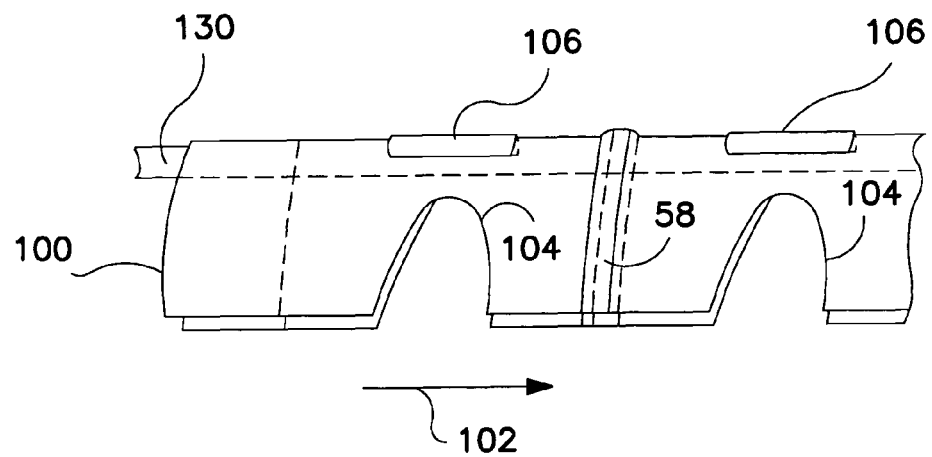
FIG. 8B is a perspective view of a machine direction process for assembling pants.
Figure 8C:
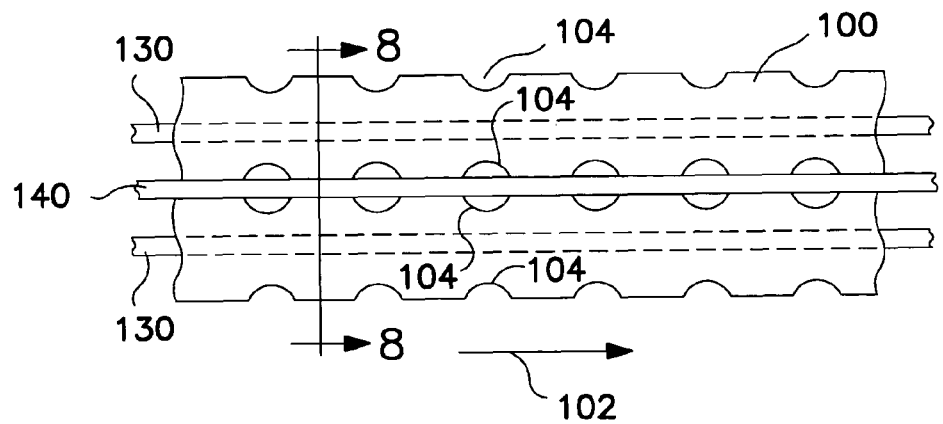
FIG. 8C is a top view of a multi-lane machine direction process for assembling pants.
Figure 8D:
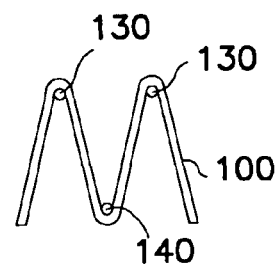
FIG. 8D is a cross-sectional view taken along line 8-8 in FIG. 8C.
Figure 9:
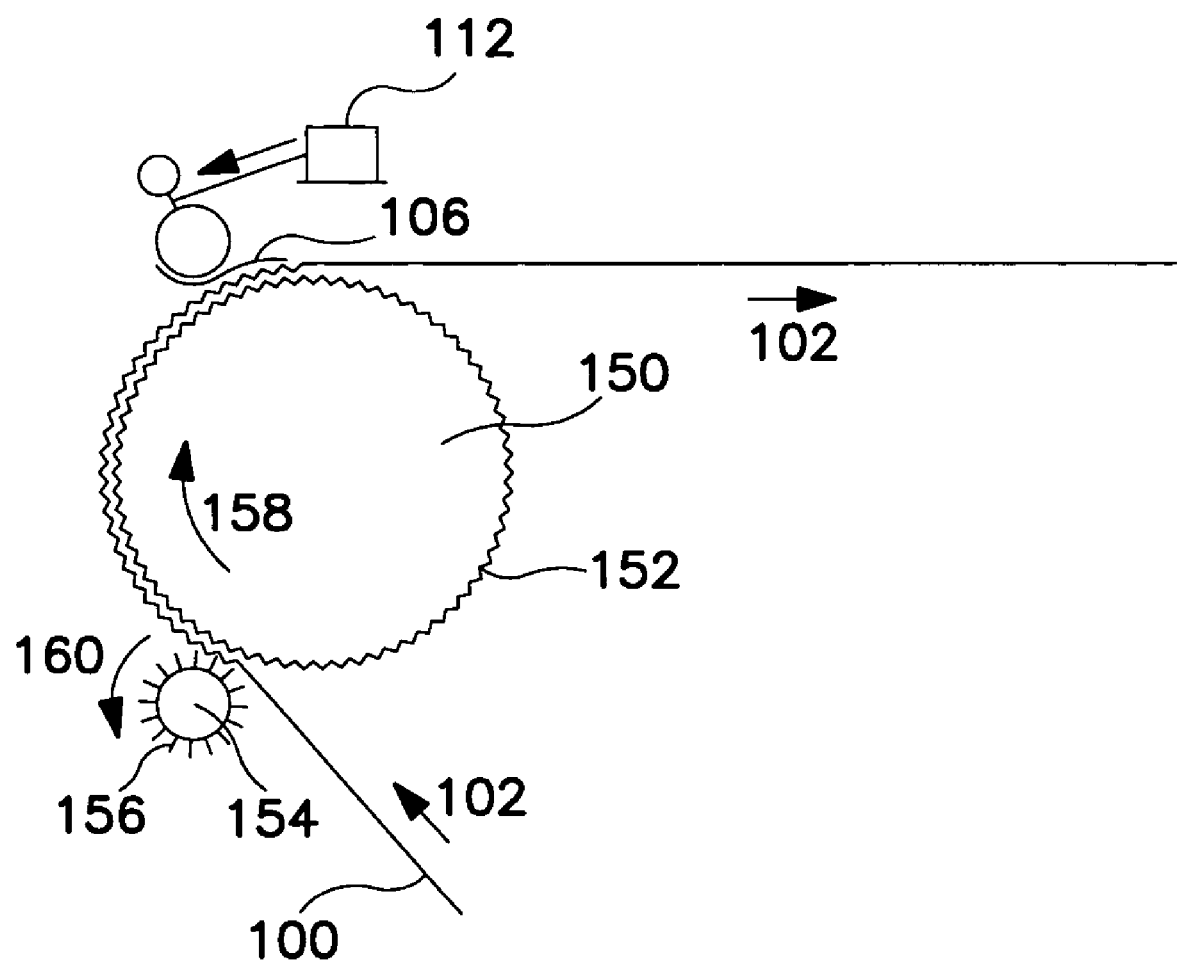
FIG. 9 is a side view of a corrugating drum for corrugating the web of FIG. 5.

In certain embodiments, the web 100 may be folded against a support structure 130 (FIGS. 8B and 8D). Examples of suitable support structures include internal support structures such as bars over which the web may be folded, or external support structures such as opposing vacuum conveyors between which the web may be folded. This folding may occur any time prior to the final product cutoff. When the process is being carried out in the machine direction, as shown in FIG. 8B, the web 100 is folded along its longitudinal centerline. The contracted crotch region 120 may be formed against the fold while the web 100 is positioned on the support structure 130. When the contraction involves application of a strip 106 or other additional piece of material, the support structure 130 within the folded area of the web 100 may provide useful opposition to the application of the strip. In particular, if the strip 106 is pre-stretched it may be helpful to have an object such as the support structure 130 against which to stretch the strip during or prior to application. Alternatively, the strip 106 may be applied to the web 100 when positioned between the web 100 and the support structure 130. Additionally, when the web 100 is folded along the longitudinal centerline, both leg openings 104 may be cut simultaneously with a single cutting action. An absorbent structure 60, if desired, can be attached to the web 100 before the web is folded, while the web is folded, or after unfolding the web. For instance, the fold of the web 100 may be inverted around an absorbent structure 60, such that a strip 106 may be applied to an inner surface of the web 100 while in a convex position over the support structure 130, or an absorbent structure 60 may be applied to the web 100 over the strip 106 after removing the web 100 from the support structure 130 and inverting the web 100 into a concave position into which the absorbent structure 60 may be inserted.

The process may also be carried out using a multi-lane production system for even greater efficiency, as illustrated in FIG. 8C. A cross-section of the multi-lane set-up is illustrated in FIG. 8D. When using the multi-lane set-up, each pant assembly is folded against a single support structure 130. The pant assemblies on a single support structure 130 are connected end-to-end or waist-to-waist, and each pant assembly is connected along at least one transverse edge 107 to another pant assembly on an adjacent support structure 130. Transversely adjacent pant assemblies may be slit apart or otherwise separated at point 140 in FIG. 8D, for example, at any suitable point during the process. For example, the support structure 130 may include upper and lower support bars, in which case point 140 may be a lower support bar, and the lane slitting may occur at point 140 or between the upper and lower support bars 130, 140; in either case, the slitting occurs along adjoining edges 107 to separate adjacent assemblies.

In particular embodiments, the strips 106 may be applied to the web 100 after contraction or pregathering of the web 100. The application of the strips 106 need not necessarily take place in conjunction with the folding process. In the machine direction, the web 100 can be pregathered by corrugating in the selected areas between the leg openings 104 by using a corrugating drum 150 (FIG. 9) in preparation for attachment of strip 106. Corrugating drums like corrugating drum 150 are known and are described, for example, in previously mentioned U.S. Pat. No. 4,397,704 issued Aug. 9, 1983 to Frick. Alternatively, a drum with discontinuous grooves that correlate with the location of strips 106 can be used. The web 100 travels around the drum 150 in the direction of arrow 158. Pressing roll 154 has teeth 156. The web 100 is pushed down into the grooves 152 by the teeth 156, thereby corrugating the web 100. Drum 150 and pressing roller 154 move in the direction of arrows 158 and 160, respectively.

Next, the strips 106 can be applied to the corrugated web 100 by a conventional cut-and-place applicator or other appropriate apparatus. Strips 106 can be attached to the web 100 using adhesive, thermal or ultrasonic bonding, or other means known in the art. Use of a corrugating drum or other device to pregather the web 100 permits the use of an unstretched elastic or of a non-elastic, non-retractive material such as a film or nonwoven material with properties similar to the web 100. Alternatively, the strip 106 may include any of the previously described materials. The strips 106 maintain the corrugation in the contracted area 120 (FIG. 6).

In the cross direction process (FIGS. 10A-12), as in the machine direction process, strips 106 can be applied to the selected areas located between the leg openings 104. In the cross direction assembly process, strips may be applied on the web 100 in an orientation essentially parallel with the longitudinal axis 48, as shown in FIG. 10A.

The application of strip 106 of elastic material can be accomplished by a variety of methods, such as by moving the distal edges of the web 100 closer together and allowing the center portion of the web to become looped using the same principles of the previously described looper drum, but with the strip 106 being applied in an orientation perpendicular to arrow 102, or by other methods as are known in the art. As with the previously described looper drum, the web 100 can be fully extended again after application of the strip 106 in order to fully adhere the strip 106 to the web 100. In alternative embodiments, the strips 106 can be applied to the web 100 by a process in which an elastic or inelastic piece of material is cut, rotated and placed onto the web 100, for example, as described in U.S. Pat. No. 5,716,478 issued Feb. 10, 1998 to Boothe et al., U.S. Pat. No. 5,759,340 issued Jun. 2, 1998 to Boothe et al. and U.S. Pat. No. 4,608,115 issued Aug. 26, 1986 to Schroth et al., all of which are herein incorporated by reference, or by any other means known in the art. Where the strip 106 is a heat contractible material or a material capable of delayed retraction, the strip can be applied to web 100 as the web travels in the direction of arrow 102 (FIG. 10A) in a flat and unlooped state.

The web 100 can be contracted elastically or inelastically by any of the previously described methods. FIG. 11 shows the web 100 after the contraction of the strips 106. The contraction of the web 100 defines contracted area 120 in the selected areas between the leg openings 104. The contracted area 120, as described more fully below, becomes the contracted crotch region 26 of the pant 10.

Figure 10B:
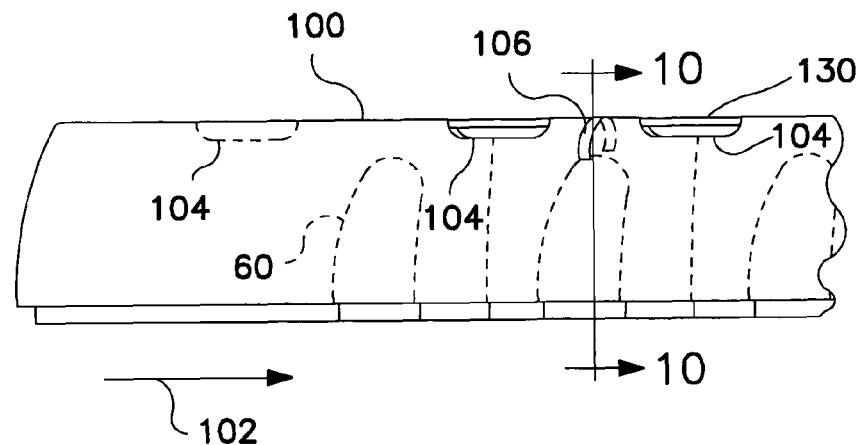
FIG. 10B is a perspective view of a cross direction process for assembling pants.

As described above, the web 100 may be folded against a support structure 130 in certain embodiments. This folding may occur any time prior to the final product cutoff. When the process is being carried out in the cross direction, as shown in FIG. 10B, the web 100 is folded perpendicular to the longitudinal centerlines of the individual garments within the web 100. The contracted crotch region may be formed while the web 100 is folded and positioned on the support structure 130, or before or after the web 100 is positioned on the support structure 130. When the contraction involves application of a strip 106 or other additional piece of material, the support structure 130 against the folded web 100 may provide useful opposition to the application of the strip 106. In particular, if the strip 106 is pre-stretched it may be helpful to have an object such as the support structure 130 against which to stretch the strip during application. In certain embodiments, such as when the support structure 130 includes opposing vacuum conveyors, two or more separate strips 106 may be applied to the web 100 on opposite sides of the fold. As explained above with respect to the machine direction process, the strip 106 may, alternatively, be positioned between the web 100 and the support structure 130 when applying the strip 106 to the web 100.

Figure 10C:
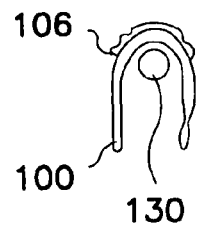
FIG. 10C is a cross-sectional view taken along line 10-10 in FIG. 10B.

Additionally, when the web 100 is folded perpendicular to the longitudinal centerline or longitudinal axis 48 of the garment assemblies, the leg openings 104 may be cut while the web 100 is on the support structure 130. An absorbent structure 60, if desired, can be attached to the web 100 before the web is folded, while the web is folded, or after unfolding the web. Alternatively, as described above with respect to the machine direction process, the web 100 may be inverted prior to attaching the absorbent structure 60 to the web 100. This folded configuration of the web 100 may facilitate easier insertion of the absorbent structure 60 since the length from the front waist edge 38 to the back waist edge 39 through the crotch region 26 may differ between the absorbent structure 60 and the garment shell 64, particularly before the crotch region 26 is contracted. Such a difference may be better accommodated when both components are folded, thus bringing the waist edges 38, 39 into close proximity to one another. As illustrated in FIG. 10C, the absorbent structure 60 need not be stretched to fit the garment shell 64, nor does the garment shell 64 have to be gathered to fit the absorbent structure, as may be required in a flat process.

Figure 10D:
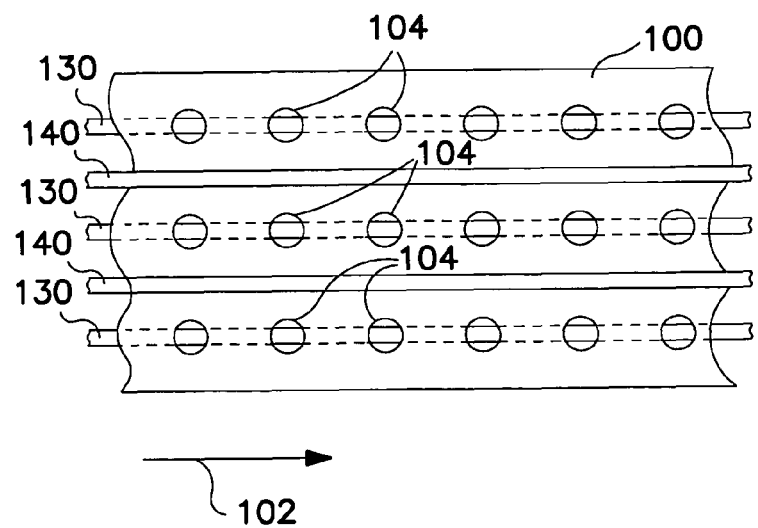
FIG. 10D is a top view of a multi-lane cross direction process for assembling pants.
Figure 12:
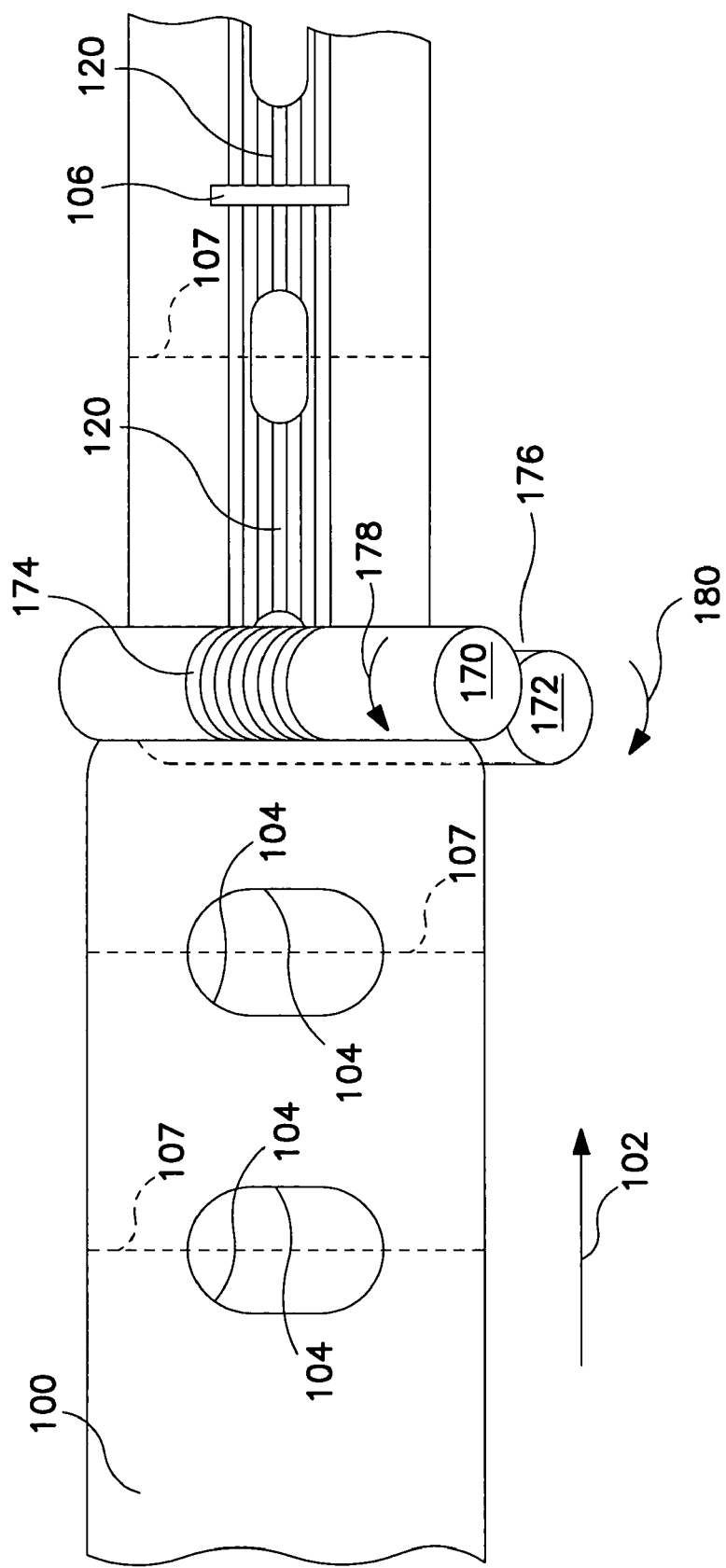
FIG. 12 is a side view of the web of FIG. 10A passing through corrugating rollers for corrugating the web of FIG. 10A.

As also described above with respect to the machine direction conveyance of the web 100, the process may also be carried out using a multi-lane production system in the cross direction conveyance, as illustrated in FIG. 10D. When using the multi-lane set-up in the cross direction, each machine-direction array of pant assemblies is folded against a single support structure 130. The pant assemblies on a single support structure 130 are connected side-to-side, and each pant assembly is connected waist-to-waist to another pant assembly on an adjacent support structure 130. The slitting apart of transversely adjacent pant assemblies may occur along the fold line (if any) between the waists of adjacent garment assemblies at any suitable point during the process.

In particular embodiments, the strips 106 are applied to the web 100 after contraction or pregathering of the web 100. In the cross direction, the web 100 can be pregathered by corrugating in the selected areas between the leg openings 104 by using intermeshing grooved rollers 170 and 172 (FIG. 12) in preparation for attachment of strip 106. Intermeshing grooved rollers like 170 and 172 are known in the art and are described, for example, in U.S. Pat. No. 5,755,902 issued May 26, 1998 to Reynolds, herein incorporated by reference. Roller 170 includes grooves 174 only in the middle portion of the roll to correspond to the desired location of the contracted area 120 on the web. The web 100 travels through nip 176 formed by rolls 170 and 172 in the direction of arrow 102. Roller 172 has complementary grooves (not shown) designed to intermesh with grooves 174 of roller 170. The web 100 is pushed into the grooves 174 by the complementary grooves on roll 172 to provide the corrugation in the contracted area 120. Rolls 170 and 172 move in the direction of arrows 178 and 180, respectively. The corrugations are held in place by attaching strips 106 on top of the corrugations.

The strip 106 can be applied to the corrugated web 100 by a cut-and-place module, or similar technology, as is commonly known in the art and can be attached to the web using thermal, ultrasonic or adhesive bonding, or any other means known in the art. The strip 106 may include an inextensible material such as a film or nonwoven material with properties similar to web 100, or may include any of the previously described materials.

In either the machine direction process or the cross direction process, the web 100 can now be cut into individual pieces, each of which will form a garment shell 64. The cutting can be accomplished by, for example, pinch cutting, shear cutting, or any other means known in the art. As another alternative, the web 100 can be provided as separate pre-cut pieces each of which pre-cut separate pieces will eventually become a single garment shell 64, so that this cutting step could be skipped and the process could start with a pre-cut piece as the web 100. FIG. 3C shows the garment shell 64 prior to folding and formation of the side seams 54. As shown and as previously mentioned with respect to FIGS. 1, 2A, and 2B the garment shell 64 can include a front region 22, a back region 24, a contracted crotch region 26, an inner surface 28, and an outer surface 30 (not shown), front waist edge 38, back waist edge 39, and waist elastic member 58. The garment shell 64 can also include strip 106. It is also contemplated that the garment shell 64 can be made upside-down, i.e., with the inner surface 28 facing downwardly (not shown). The garment shell 64 can then be folded and the side seams 54 formed by any conventional method known in the art to form the pant 10 (without an absorbent structure). It is contemplated that the step of contracting the web 100 can occur either before or after the step of cutting into individual garment shells 64, and also before or after the formation of the side seams 54.

Figure 3D:
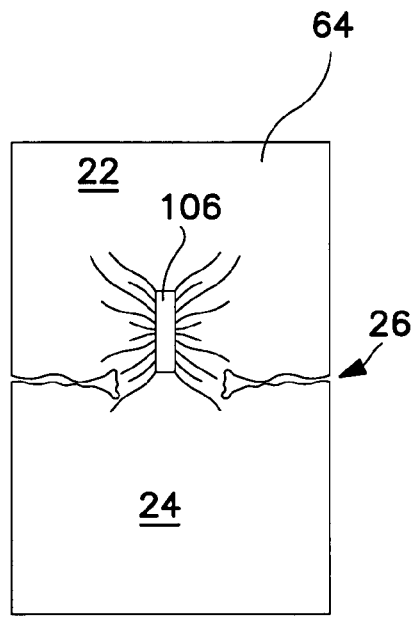
FIGS. 3D-3G are plan views of garments similar to the garment shown in FIG. 3C but with alternative strip configurations in the contracted crotch region.
Figure 3E:
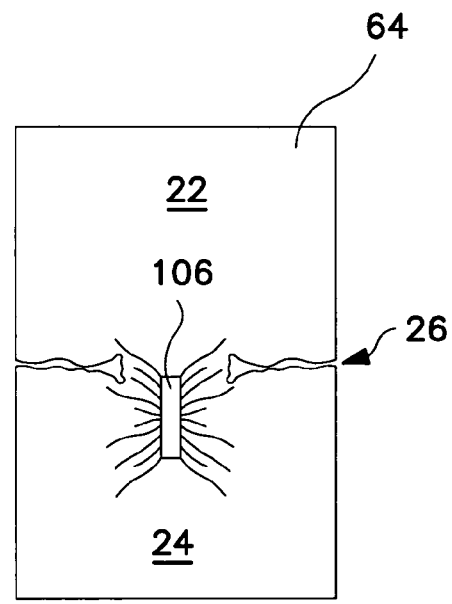
Figure 3F:
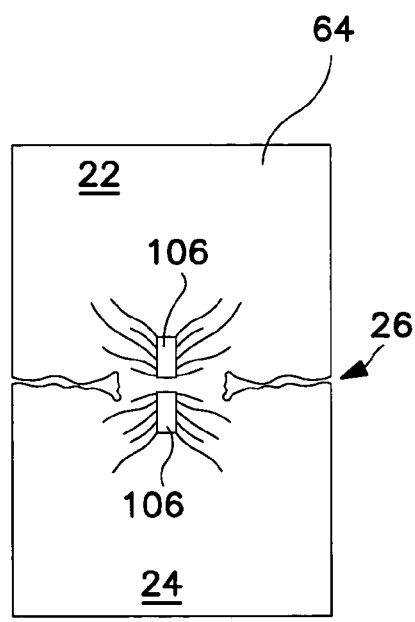
Figure 3G:
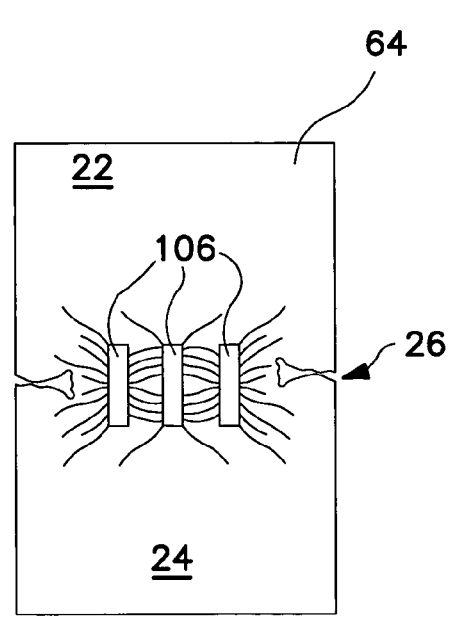

In either the machine direction process or the cross direction process, in alternative embodiments, the strip 106 need not be a single strip of material. In particular embodiments, elastic strands or ribbons as are known in the art can be used instead of a single strip of material for strip 106. The elastic strands or ribbons can be straight or curved. Alternatively, the contracted crotch region 26 may include one or more strips 106 longitudinally offset, such as shown in FIGS. 3D and 3E, or multiple strips 106 arranged in a segmented manner, either spaced apart longitudinally (FIG. 3F) or spaced apart transversely (FIG. 3G). In certain embodiments, the strip may be, at most, one-third the length of the garment shell when the garment shell is in a laid-flat, fully extended, namely uncontracted, condition. In addition, in the embodiments in which the web is corrugated or otherwise gathered, it is contemplated that instead of attaching a strip 106, the corrugation or gathers in the contracted area 120 can be maintained by fusing or bonding the corrugations together in the selected areas between the leg openings 104. The corrugations can be bonded to themselves to hold them in place by adhesive, thermal, or pressure bonding, or by any other means known in the art.

In the machine direction process, the strip 106 need not be a separate piece of material applied to the web 100. Instead, the web 100 may include an integral elastic zone aligned along the machine direction center line, instead of strip 106, with the elastic zone active in only the crotch region. Elasticization of only the crotch region of the pant may be achieved by, for example, an elastic laminate structure in which the elastic is attached to the laminate using an intermittent adhesive. Intermittent adhesive application would allow the elastic to snap back from non-adhesive zones, which would be uncontracted as a result; contracted, adhesive-bearing zones can be located only in the crotch region of the garment. As an alternative, the elastic nature of certain regions may be inactivated by chopping or overbonding the elastic or other methods known in the art, for example, as described in U.S. Pat. No. 6,248,097 issued Jun. 19, 2001 to Beitz, herein incorporated by reference.

Referring to FIGS. 2A, 2B, 3A, and 3B in particular embodiments, an absorbent structure 60 is included in the pant 10. The absorbent structure 60 can be introduced into the pant 10 in any suitable manner known in the art. In particular embodiments, the absorbent structure 60 can be placed on top of the contracted crotch region 26 on the inner surface 28 of the garment shell 64, either prior to formation of side seams 54 or after side seams 54 are made. It is also contemplated, however, that the absorbent structure 60 can be attached prior to contracting and/or cutting the web 100. Where the absorbent structure 60 is added to the pant 10 prior to formation of side seams 54, cut and place methods such as are known in the art may be used. Alternatively, for a closed pant (i.e., side seams already formed), the absorbent structure 60 may be inserted into the pant such as by the method described in the PCT Publication WO 02/52967 by Rabe, et al., or by other means as may be known in the art. The absorbent structure 60 can be attached to the garment shell 64 at the front waist edge 38 and back waist edge 39, or at some point below the front waist edge 38 and back waist edge 39 on the front region 22 and back region 24. Additionally or alternatively, the absorbent structure 60 can be attached in the contracted crotch region 26. The attachment can be accomplished by ultrasonic or adhesive bonding, or any other suitable method known in the art. As shown in FIGS. 2A and 2B, attachment to the front and back regions 22 and 24 provides for a loose fit of shell 64 in the contracted crotch region 26, while the absorbent structure 60 is still held close to the body.

In particular embodiments, the absorbent structure 60 is stretchable or elasticizable in order to provide the desired close to the body fit for the absorbent structure 60 while the garment shell 64 hangs loosely. Alternatively, a suspension system for the absorbent structure may be required to provide a loose fit for the garment shell 64, such as described in U.S. Pat. No. 6,168,585 issued Jan. 2, 2001 to Cesco-Cancian, herein incorporated by reference.

The garment shell 64 with the absorbent structure 60 can then be folded and the side seams 54 formed by any conventional method known in the art to form the pant 10, as shown in FIGS. 2A and 2B. After folding the garment shell 64 and forming the side seams 54 (with or without an absorbent structure 60), if a temporarily inhibited elastic or latent elastic is used as the waist elastic 58, it may need to be activated to restore the elasticity. Alternatively, the elastics may be activated prior to seaming.

The various components of the pant can be connected together by any means known to those skilled in the art such as, for example, adhesive, thermal and/or ultrasonic bonds, pressure bonds and also sewing and other methods used in durable garment manufacturing. Most of the components may be connected using ultrasonic bonding for improved manufacturing efficiency and reduced raw material costs. For example, in particular embodiments, the side seams 54 are made using ultrasonic bonding. Certain garment manufacturing equipment which is readily known and understood in the art, including frames and mounting structures, ultrasonic and adhesive bonding devices, transport conveyors, transfer rolls, guide rolls, tension rolls, and the like, have not been shown in the Figures.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. For example, features described in relation to one embodiment may be incorporated into any other embodiment of the invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

What is claimed is:

1. A method of making a pant having a first region, a second region, a crotch region extending from the first region to the second region, side seams and hanging legs, the method comprising:
   providing a continuous web comprising a plurality of pant assemblies connected to one another;
   folding the continuous web around an internal support structure;
   contracting at least one of the plurality of pant assemblies of the web in at least one selected area to define a contracted crotch area within the crotch region;
   cutting said at least one of the plurality of folded pant assemblies with a single cut to define two slits of a single one of said folded pant assemblies and a separation between the first region and the second region while maintaining a seamless connection between the first region and the second region in the contracted crotch area, wherein cutting the at least one of the plurality of folded pant assemblies does not result in the removal of any portion of the at least one of the plurality of folded pant assemblies; and
   attaching the first region and the second region together to form boxer shorts having the side seams and hanging legs, wherein each of the slits defines a respective leg opening of the pant.

2. The method of claim 1, comprising applying at least one strip to the folded web in the at least one selected area.

3. The method of claim 1, comprising conveying the web in a machine direction.

4. The method of claim 1, comprising conveying the web in a cross direction.

5. A method of making a pant having side seams and hanging legs, comprising:
   providing a continuous web comprising a plurality of pant assemblies connected to one another, each pant assembly having a front region, a back region, and a crotch region extending between the front region and the back region;
   folding the continuous web against an internal support structure;
   contracting at least one of the plurality of pant assemblies of the web in at least one selected area to define a contracted crotch area within the crotch region, wherein the crotch area is contracted relative to the front region and the back region;
   cutting said at least one of the folded plurality of pant assemblies with a single cut to define two openings of a single one of said folded pant assemblies and a separation between the front region and the back region while maintaining a seamless connection between the front region and the back region in the contracted crotch area;
attaching an absorbent structure to the web; and
attaching the front region and the back region together to form boxer shorts having side seams and hanging legs.

6. The method of claim 5, comprising attaching the absorbent structure to the web while the web is folded.

7. The method of claim 5, comprising attaching the absorbent structure to the web prior to folding the web.

8. The method of claim 5, further comprising:
unfolding the web; and
attaching the absorbent structure to the web after unfolding the web and before attaching the front region and back region together to form the side seams and hanging legs.

9. The method of claim 5, comprising conveying the web in a machine direction.

10. The method of claim 5, comprising conveying the web in a cross direction.

11. A method of making a pant having a first region, a second region, a crotch region extending between the first region and the second region, side seams and hanging legs, the method comprising:
conveying a continuous web of a plurality of pant assemblies connected to one another in a machine direction;
folding the continuous web against at least two internal support structures wherein the at least two internal support structures are parallel to each other and parallel to a direction in which the web is conveyed, wherein each machine direction conveyed plurality of pant assemblies is folded against a single one of the at least two internal support structures;
contracting the web in at least one selected area in each pant assembly to define a contracted crotch area within the crotch region;
cutting at least one portion of the folded web with a single cut to form two openings of a single one of each pant assembly, wherein the at least one cut portion further defines a separation between the first region and the second region in each pant assembly while maintaining a seamless connection between the first region and the second region in the contracted crotch area; and
attaching the first region and the second region of each pant assembly together to form boxer shorts having the side seams and hanging legs.

12. The method of claim 1, further comprising refastenably attaching an absorbent structure to the pant for allowing replacement of the absorbent structure when soiled.

13. The method of claim 1, wherein the slits have a longitudinal component and a transverse component, the transverse component being generally perpendicular to and intersecting the longitudinal component.

14. The method of claim 5, wherein each of the openings has an interior end and further comprising cutting a reinforcing cut-out at the interior end of at least one of the two openings.

15. The method of claim 14, wherein cutting the reinforcing cut-out comprises cutting a circular cut-out.

\* \* \* \* \*